United States Patent

Tsuda

[11] Patent Number: 5,906,581
[45] Date of Patent: May 25, 1999

[54] APPARATUS FOR EVALUATING EXERCISE FUNCTION OF PERSON

[75] Inventor: Hideichi Tsuda, Komaki, Japan

[73] Assignee: Colin Corporation, Komaki, Japan

[21] Appl. No.: 08/769,442

[22] Filed: Dec. 19, 1996

[51] Int. Cl.[6] ................................................... A61B 5/00
[52] U.S. Cl. .......................... 600/485; 600/490; 600/494; 600/500; 600/520
[58] Field of Search ................................... 600/483, 484, 600/485, 500, 501, 502, 526, 490, 493, 495, 492, 481, 520

[56] References Cited

U.S. PATENT DOCUMENTS

| | | | |
|---|---|---|---|
| 3,675,640 | 7/1972 | Gatts . | |
| 4,347,851 | 9/1982 | Jundanian | 600/485 |
| 4,404,974 | 9/1983 | Titus | 600/485 |
| 4,617,937 | 10/1986 | Peel et al. . | |
| 4,789,153 | 12/1988 | Brown | 272/73 |
| 5,435,315 | 7/1995 | McPhee et al. . | |
| 5,524,637 | 6/1996 | Erickson | 600/592 |
| 5,560,365 | 10/1996 | Ogura | 600/499 |
| 5,584,298 | 12/1996 | Kabal | 600/485 |

FOREIGN PATENT DOCUMENTS

| | | |
|---|---|---|
| 2-694-421 | 2/1994 | France . |
| B-2-4-67453 | 10/1992 | Japan . |
| B-2-4-67454 | 10/1992 | Japan . |
| B-2-7-47053 | 5/1995 | Japan . |
| 2-257-795 | 1/1993 | United Kingdom . |
| WO-85/00279 | 1/1985 | WIPO . |
| WO 90/08361 | 7/1990 | WIPO . |
| WO-95/07650 | 3/1995 | WIPO . |
| WO-95/18564 | 7/1995 | WIPO . |

OTHER PUBLICATIONS

P. Schwindke et al.; "An Apparatus for Full Automatic Measurement of Pulse Frequency, Blood Presssure, and Pulse–Pressure–Products at Rest and When Stressed" *Biomedizinische Technik* vol. 22, No. 11/77 Nov. 1977, Berlin Germany.

*Primary Examiner*—Robert L. Nasser
*Attorney, Agent, or Firm*—Oliff & Berridge, PLC

[57] ABSTRACT

An apparatus for evaluating an exercise function of a person who undergoes an exercise load, including a pulse-rate measuring device which successively measures a pulse rate of the person in synchronism with a heartbeat of the person, a blood-pressure measuring device which successively and non-invasively measures a blood pressure of the person in synchronism with the heartbeat of the person, a first calculating device which successively calculates a product of the pulse rate and the blood pressure in synchronism with the heartbeat of the person, a second calculating device which calculates a total energy produced by the person after application of the exercise load to the person is started and before the products successively calculated by the first calculating device increase up to a target value, and a display device which displays an evaluation value of the exercise function of the person based on the total energy calculated by the second calculating device.

21 Claims, 14 Drawing Sheets

APPARATUS FOR EVALUATING EXERCISE FUNCTION OF PERSON

BACKGROUND OF THE INVENTION

1. Field of the Invention

The present invention relates to an apparatus which evaluates an exercise function of a person who undergoes an exercise load.

2. Related Art Statement

It is generally known that when a first person having a high circulatory-organ function or performance and a second person having a low one undergo an exercise load, the range of change of an index (e.g., pulse rate) indicative of the circulatory-organ function of the first person is smaller than that of the second person. Additionally, after persons undergo an exercise load, various patterns of time-wise change of the index are obtained depending upon respective degrees of the circulatory-organ function of those persons. Hence, for example, before and after an exercise load is applied to a person, or just after the application of an exercise load to a person and a certain time after, a pulse rate measurement is carried out on the person, so that the exercise function of the person can be evaluated by the comparison between the change of the measured pulse rate values and a standard change value.

However, in the case where the exercise function of a person is evaluated as described above, it is very cumbersome to measure the pulse rate of the person before and after the application of an exercise load, or just after the application of an exercise load and a certain time after. Additionally, the above-identified prior method requires the person to select, according to a look-up table, one of different exercise-function index values which corresponds to the measured pulse rate change. Thus, it is more or less difficult for a person who is not familiar with the evaluation method to evaluate his or her exercise function by himself or herself.

In the above-indicated situation, the Assignee of the present application had proposed an exercise apparatus which simultaneously displays an actual curve representing an actual time-wise change of pulse rate values measured from a person who is undergoing a predetermined exercise load, and a standard curve, so that an observer can evaluate the exercise function of the person by comparing the two curves with each other, and an apparatus which displays, as an exercise-function index, a total energy produced by a person after the application of an exercise load to the person is started and before pulse rate values measured from the person increase up to a target value. The two apparatuses are disclosed in Japanese Patent Applications laid open for opposition purposes under Publication Nos. 4(1982)67453 and 4-67454, respectively. Each of the two apparatuses enables a person to see more objectively and more easily his or her exercise function.

In the above prior exercise apparatuses, pulse rate or blood pressure is utilized for evaluating the exercise function of a person. However, pulse rate or blood pressure cannot accurately indicate "internal" load applied to person's body. Therefore, the exercise function of a person cannot be accurately evaluated by utilizing those indexes. In particular, in the case where an inflatable cuff is used to measure the blood pressure of a person, blood pressure values cannot be measured at a cyclic period shorter than several tens of seconds. Therefore, it is difficult to measure a sufficiently great number of blood pressure values for providing an actual curve to be compared with a standard curve, or it is difficult to judge with sufficiently high accuracy whether or not the measured blood pressure values have increased up to a target value. Thus, each of the prior exercise apparatuses cannot enable a person to evaluate his or her exercise function with satisfactorily high accuracy.

SUMMARY OF THE INVENTION

It is therefore an object of the present invention to provide an apparatus which evaluates, with accuracy, an exercise function of a person.

The above object has been achieved by the present invention. According to a first aspect of the present invention, there is provided an apparatus for evaluating an exercise function of a person who undergoes an exercise load, comprising a pulse-rate measuring device which successively measures a pulse rate of the person in synchronism with a heartbeat of the person, a blood-pressure measuring device which successively and non-invasively measures a blood pressure of the person in synchronism with the heartbeat of the person, a first calculating device which successively calculates a product of the pulse rate and the blood pressure in synchronism with the heartbeat of the person, a second calculating device which calculates a total energy produced by the person after application of the exercise load to the person is started and before the products successively calculated by the first calculating device increase up to a target value, and a display device which displays an evaluation value of the exercise function of the person based on the total energy calculated by the second calculating device.

In the evaluating apparatus in accordance with the first aspect of the invention, the display device displays an evaluation value of the exercise function of a person based on the total energy produced by the person after the application of an exercise load to the person is started and before the pressure-rate products successively calculated by the first calculating device increase up to a target value. Since the pressure-rate products accurately indicate the internal load applied to the person, the evaluation value displayed by the display device accurately indicates the exercise function of the person. In addition, the blood-pressure (BP) measuring device successively and non-invasively measures the BP values of the person in synchronism with the heartbeat of the person, and accordingly the first calculating device successively calculates the pressure-rate products in synchronism with the heartbeat of the patient. That is, the first calculating device calculates, without delay, the current pressure-rate product and accordingly it is judged without delay that the pressure-rate products successively calculated by the first calculating device have increased up to the target value. Therefore, the exercise function of the person is evaluated with high accuracy.

According to a preferred feature of the first aspect of the invention, the blood-pressure measuring device comprises a pressing device which provides a pressing force to press a body portion of the person, a pressing-force changing device which changes the pressing force of the pressing device, standard-blood-pressure determining means for determining a standard blood pressure of the person based on a heartbeat-synchronous wave obtained while the pressing force of the pressing device is changed by the pressing-force changing device, a pressure-pulse-wave sensor adapted to be pressed against an artery of the person via a skin tissue above the artery so as to detect a magnitude of a pressure pulse wave produced from the artery in synchronism with the heartbeat of the person, relationship determining means for determining a relationship between blood pressure and magnitude of pressure pulse wave, based on the standard blood pressure determined by the standard-blood-pressure determining means and the magnitude of the pressure pulse wave detected by the pressure pulse wave sensor, and blood-pressure estimating means for successively estimating a blood pressure of the person, based on a magnitude of each of a plurality of heartbeat-synchronous pulses of the pressure pulse wave detected by the pressure pulse wave sensor, according to the relationship determined by the relationship determining means. A standard BP value determined by the standard-BP determining means is highly reliable, and a relationship between BP value and magnitude of pressure pulse wave is determined based on the highly reliable standard BP value and a magnitude of a pressure pulse wave detected by the pressure pulse wave sensor. The BP estimating means successively estimates a BP value of the person, based on a magnitude of each of a plurality of heartbeat-synchronous pulses of an actual pressure pulse wave detected by the pressure pulse wave sensor, according to the thus determined relationship between BP value and magnitude of pressure pulse wave. Thus, the estimated BP values, successively obtained in synchronism with the heartbeat of the person, enjoy a considerably high accuracy.

According to another feature of the first aspect of the invention, the pressing device comprises an inflatable cuff adapted to be wound around the body portion of the person, the pressing-force changing device comprising a cuff-pressure changing device which changes a fluid pressure in the cuff, the standard-blood-pressure determining means comprising means for determining the standard blood pressure of the person based on a variation of respective amplitudes of a plurality of heartbeat-synchronous pulses of the heartbeat-synchronous wave which is a pressure oscillation produced in the cuff while the pressure of the cuff is changed by the cuff-pressure changing device.

According to another feature of the first aspect of the invention, the pressing device comprises an inflatable cuff adapted to be wound around the body portion of the person, the pressing-force changing device comprising a cuff-pressure changing device which changes a fluid pressure in the cuff, the standard-blood-pressure determining means comprising means for determining the standard blood pressure of the person based on a fluid pressure of the cuff at a time when a Korotkoff sound is first detected, or last detected, from the body portion while the pressure of the cuff is changed by the cuff-pressure changing device.

According to another feature of the first aspect of the invention, the pressure pulse wave sensor comprises a flat surface adapted to be pressed against the artery of the person via the skin tissue, a plurality of pressure sensing elements arranged in the flat surface, and a flat-surface pressing device which presses the flat surface against the artery via the skin tissue, and the blood-pressure measuring device comprises means for controlling the flat-surface pressing device to press the flat surface against the artery via the skin tissue such that a portion of a wall of the artery is flattened under the flat surface and the skin tissue. In this case, since a portion of the wall of the artery is flattened under the flat surface in which the plurality of pressure sensing elements are provided, the pressure pulse wave (PPW) detected by each of the pressure sensing elements is least influenced by the tensile force of the arterial wall. Thus, the detected PPW enjoys a high accuracy and accordingly the BP-PPW relationship determined based on the detected PPW enjoys a high accuracy. In addition, the estimated BP values and the calculated pressure-rate products also enjoy a high accuracy.

According to another feature of the first aspect of the invention, the standard-blood-pressure determining means comprises means for determining the standard blood pressure of the person, before the application of the exercise load to the person is started, and the relationship determining means comprises means for determining the relationship between blood pressure and magnitude of pressure pulse wave, based on the standard blood pressure determined by the standard-blood-pressure determining means and the magnitude of the pressure pulse wave detected by the pressure pulse wave sensor before the application of the exercise load to the person is started. In the case where the BP-PPW relationship is determined just before the commencement of the exercise-load control operation of the control device, estimated BP values are obtained with higher accuracy according to the new BP-PPW relationship and accordingly pressure-rate products are calculated with higher accuracy.

According to another feature of the first aspect of the invention, the evaluating apparatus further comprises an exercise-load applying device which applies the exercise load to the person, an exercise-load changing device which changes the exercise load applied to the person by the exercise-load applying device, and judging means for judging whether the products successively calculated by the first calculating device have increased up to the target value, the exercise-load changing device zeroing, when the judging means makes a positive judgment, the exercise load applied to the person by the exercise-load applying device. In this case, the burden applied to the person for evaluating his or her exercise function is minimized.

According to another feature of the first aspect of the invention, the exercise-load applying device comprises a generator which includes a rotary member and which generates an electric power when the rotary member is rotated by the person, and the second calculating device comprises means for calculating the total energy based on a total energy produced by the generator after the application of the exercise load to the person is started and before the products successively calculated by the first calculating device increase up to the target value. In this case, both the application of the exercise load to the person and the calculation of the total energy produced by the person are carried out by using the generator. Thus, the present apparatus enjoys a simplified construction and a reduced production cost.

According to another feature of the first aspect of the invention, the display device comprises means for displaying the evaluation value comprising at least one of the total energy calculated by the second calculating device and an exercise-function index value corresponding to the total energy.

According to a second aspect of the present invention, there is provided an apparatus for evaluating an exercise function of a person who undergoes a predetermined exercise load, comprising a pulse-rate measuring device which successively measures a pulse rate of the person in synchronism with a heartbeat of the person, a blood-pressure measuring device which successively and non-invasively measures a blood pressure of the person in synchronism with the heartbeat of the person, a calculating device which successively calculates a pressure-rate product as a product of the pulse rate and the blood pressure, in synchronism with the heartbeat of the person, a first memory device which stores a first curve which represents a standard time-wise change of pressure-rate products and which corresponds to the predetermined exercise load, and a display device which simultaneously displays the first curve and a second curve representing an actual time-wise change of the pressure-rate products successively calculated by the calculating device, so that an observer can compare the first curve and the second curve with each other.

In the evaluating apparatus in accordance with the second aspect of the invention, the display device simultaneously displays the first or standard curve and the second or actual curve representing the actual time-wise change of the pressure-rate products successively calculated by the calculating device, so that an observer can compare the first curve and the second curve with each other. Since the pressure-rate products accurately indicate the internal load applied to the person, the observer can evaluate with high accuracy his or her exercise function by the comparison of the first and second curves. In addition, the blood-pressure (BP) measuring device successively and non-invasively measures the BP values of the person in synchronism with the heartbeat of the person, and accordingly the calculating device successively calculates the pressure-rate products in synchronism with the heartbeat of the patient. That is, the BP measuring device measures a sufficiently great number of blood pressure values which are utilized for providing the second or actual curve to be compared with the first or standard curve. Therefore, the person can evaluate his or her exercise function with high accuracy.

The evaluating apparatus in accordance with the second aspect of the invention may comprise one or more of the above-described features of the evaluating apparatus in accordance with the first aspect of the invention.

Additionally, according to a preferred feature of the second aspect of the invention, the evaluating apparatus further comprises a second memory device which stores the second curve, the display device comprises means for displaying the second curve stored in the second memory device, in addition to the first curve and a following second curve representing an actual time-wise change of pressure-rate products successively calculated by the calculating device in a following exercise-function evaluation, so that the observer can compare the second curve, the first curve, and the following second curve with one another. In this case, the observer who may be the person being evaluated can see the difference between the two second or actual curves and thereby recognize the change of the person's exercise function.

According to another feature of the second aspect of the invention, the evaluating apparatus further comprising an exercise-load applying device which applies an exercise load to the person, and an exercise-load changing device which changes the exercise load applied to the person by the exercise-load applying device, to the predetermined exercise load, according to a predetermined exercise-load pattern. For example, the exercise-load changing device may increase the exercise load at a predetermined rate according to the exercise-load pattern.

According to a third aspect of the present invention, there is provided an apparatus for evaluating an exercise function of a person who undergoes a predetermined exercise load, comprising a pulse-rate measuring device which successively measures a pulse rate of the person in synchronism with a heartbeat of the person, a blood-pressure measuring device which successively and non-invasively measures a blood pressure of the person in synchronism with the heartbeat of the person, a calculating device which successively calculates a pressure-rate product as a product of the pulse rate and the blood pressure, in synchronism with the heartbeat of the person, a memory device which stores a first curve which represents a standard time-wise change of pressure-rate products and which corresponds to the predetermined exercise load, and a display device which displays an evaluation value of the exercise function of the person based on a correlation coefficient between the first curve and a second curve representing an actual time-wise change of the pressure-rate products successively calculated by the calculating device.

In the evaluating apparatus in accordance with the third aspect of the invention, the display device displays an evaluation value of the exercise function of the person based on a correlation coefficient between the first curve and the second curve representing the actual time-wise change of the pressure-rate products successively calculated by the calculating device. Since the pressure-rate products accurately indicate the internal load applied to the person, the evaluation value displayed by the display device accurately indicates the exercise function of the person. In addition, the blood-pressure (BP) measuring device successively and non-invasively measures the BP values of the person in synchronism with the heartbeat of the person, and accordingly the calculating device successively calculates the pressure-rate products in synchronism with the heartbeat of the patient. That is, the BP measuring device measures a sufficiently great number of blood pressure values which are utilized for providing the second or actual curve to be compared with the first or standard curve. Therefore, the person can evaluate his or her exercise function with high accuracy.

The evaluating apparatus in accordance with the third aspect of the invention may comprise one or more of the above-described features of the evaluating apparatus in accordance with the first aspect of the invention.

Moreover, according to a preferred feature of the third aspect of the invention, the display device comprises means for displaying the evaluation value comprising at least one of the correlation coefficient between the first curve and the second curve and an exercise-function index value corresponding to the correlation coefficient.

According to a fourth aspect of the present invention, there is provided an apparatus for evaluating an exercise function of a person who undergoes a predetermined exercise load, comprising a pulse-rate measuring device which successively measures a pulse rate of the person in synchronism with a heartbeat of the person, a blood-pressure measuring device which successively and non-invasively measures a blood pressure of the person in synchronism with the heartbeat of the person, a calculating device which successively calculates a pressure-rate product as a product of the pulse rate and the blood pressure, in synchronism with the heartbeat of the person, a memory device which stores a first curve which represents a standard time-wise change of pressure-rate products and which corresponds to the predetermined exercise load, and a display device which displays an evaluation value of the exercise function of the person based on an area defined by, and between, the first curve and a second curve representing an actual time-wise change of the pressure-rate products successively calculated by the calculating device.

In the evaluating apparatus in accordance with the fourth aspect of the invention, the display device displays an evaluation value of the exercise function of the person based on an area defined by, and between, the first curve and the second curve representing the actual time-wise change of the pressure-rate products successively calculated by the calculating device. Since the pressure-rate products accurately indicate the internal load applied to the person, the evaluation value displayed by the display device accurately indicates the exercise function of the person. In addition, the blood-pressure (BP) measuring device successively and non-invasively measures the BP values of the person in synchronism with the heartbeat of the person, and accordingly the calculating device successively calculates the pressure-rate products in synchronism with the heartbeat of the patient. That is, the BP measuring device measures a sufficiently great number of blood pressure values which are utilized for providing the second or actual curve to be compared with the first or standard curve. Therefore, the person can evaluate his or her exercise function with high accuracy.

The evaluating apparatus in accordance with the fourth aspect of the invention may comprise one or more of the above-described features of the evaluating apparatus in accordance with the first aspect of the invention.

Additionally, according to a preferred feature of the fourth aspect of the invention, the display device comprises means for displaying the evaluation value comprising at least one of the area defined by and between the first curve and the second curve and an exercise-function index value corresponding to the area.

BRIEF DESCRIPTION OF THE DRAWINGS

The above and optional objects, features, and advantages of the present invention will better be understood by reading the following detailed description of the preferred embodiments of the invention when considered in conjunction with the accompanying drawings, in which.

DETAILED DESCRIPTION OF THE PREFERRED EMBODIMENTS

Referring to FIGS. 1 to 7, there will be described an exercise apparatus 4 having an exercise-load changing function to which the present invention is applied. The exercise apparatus 4 includes an ergometer 6 having a pair of pedals 65 which are rotated by a pair of feet of a person such as a patient, and a blood-pressure (BP) measuring device 8 which successively measures a BP value of the person in synchronism with the heartbeat of the person.

Figure 1:
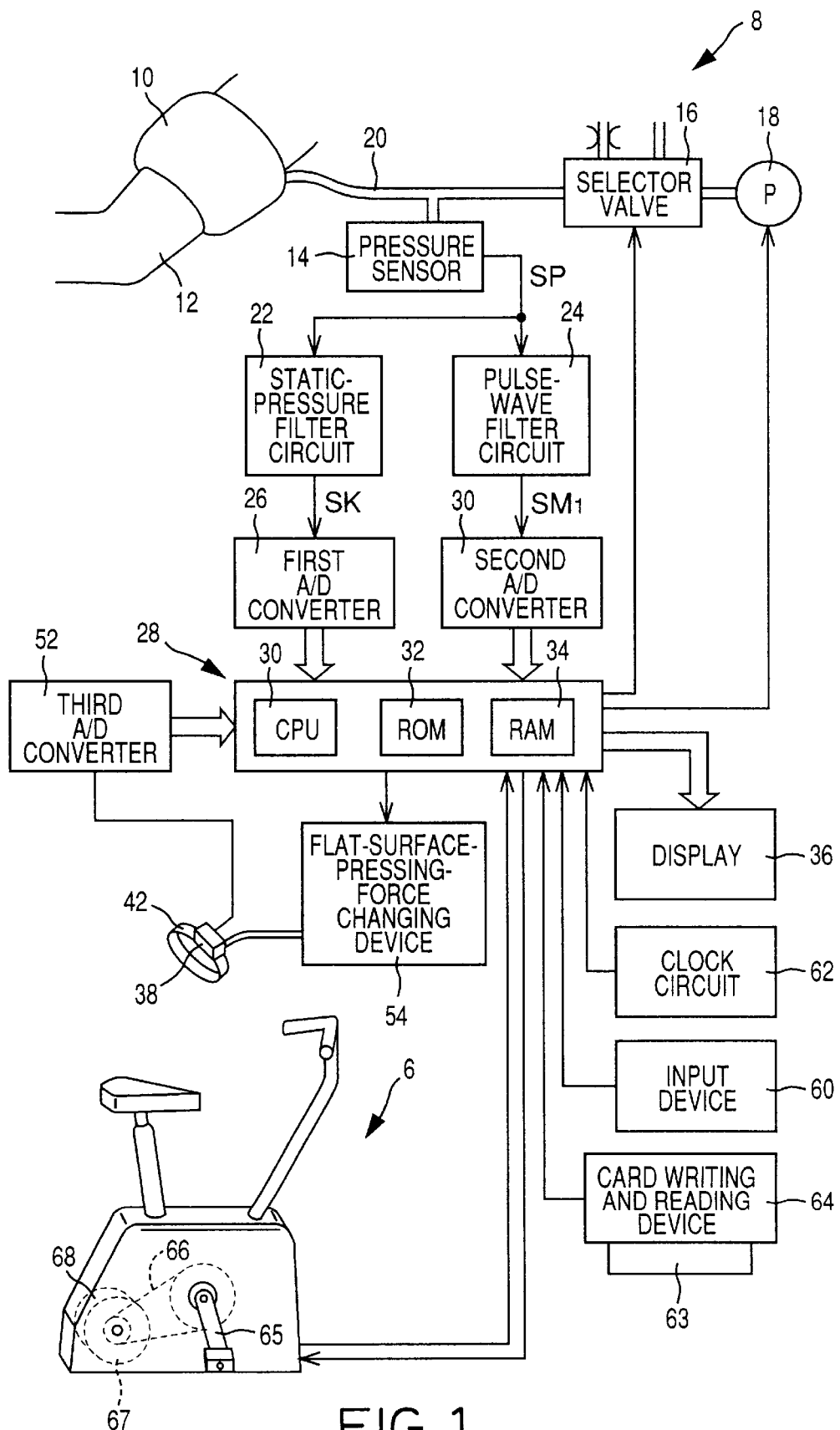
FIG. 1 is a diagrammatic view of an exercise apparatus having an exercise-load changing function to which the present invention is applied.

In FIG. 1, the BP measuring device 8 includes an inflatable cuff 10 having a rubber bag and a band-like cloth bag in which the rubber bag is accommodated. The cuff 10 is wound around, e.g., an upper arm 12 of a patient. The cuff 10 is connected via piping 20 to a pressure sensor 14, a selector valve 16, and a first air pump 18. The selector valve 16 is selectively placed, under control of an electronic control device 28, in a first state in which the valve 16 permits pressurized air to be supplied from the air pump 18 to the cuff 10 to increase the pressure of the cuff 10 (hereinafter, referred to as the "cuff pressure"), a second state in which the valve 16 causes the cuff 10 to be deflated slowly, and a third state in which the valve 16 causes the cuff 10 to be deflated quickly.

The pressure sensor 14 detects the cuff pressure (i.e., pressure in the cuff 10), and generates a pressure signal, SP, representing the detected cuff pressure. The pressure signal SP is supplied to each of a static-pressure filter circuit 22 and a pulse-wave filter circuit 24. The static-pressure filter circuit 22 includes a low-pass filter which extracts, from the pressure signal SP, a cuff-pressure signal, SK, representing a static or direct-current component of the pressure signal SP. The cuff-pressure signal SK is supplied via a first analog-to-digital (A/D) converter 26 to the control device 28.

The pulse-wave filter circuit 24 includes a band-pass filter which extracts, from the pressure signal SP, a pulse-wave signal, $SM_1$, representing an oscillating or alternating-current component of the pressure signal SP, based on a frequency characteristic of the signal $SM_1$. The pulse-wave signal $SM_1$ is supplied via a second A/D converter 30 to the control device 28. The oscillating or alternating-current component represented by the pulse-wave signal $SM_1$ corresponds to an oscillatory pressure wave, i.e., pulse wave which is produced from a brachial artery (not shown) of patient's upper arm 12 in synchronism with the heartbeat of the patient and is propagated via skin tissue to the cuff 10. This pulse wave is referred to as the "cuff pulse wave (CPW)" to be distinguished from a "pressure pulse wave (PPW)" which will be explained later. In the present embodiment, the cuff 10, the pressure sensor 14, and the pulse-wave filter circuit 24 cooperate with one another to provide a cuff pulse wave (CPW) sensor.

Figure 5:
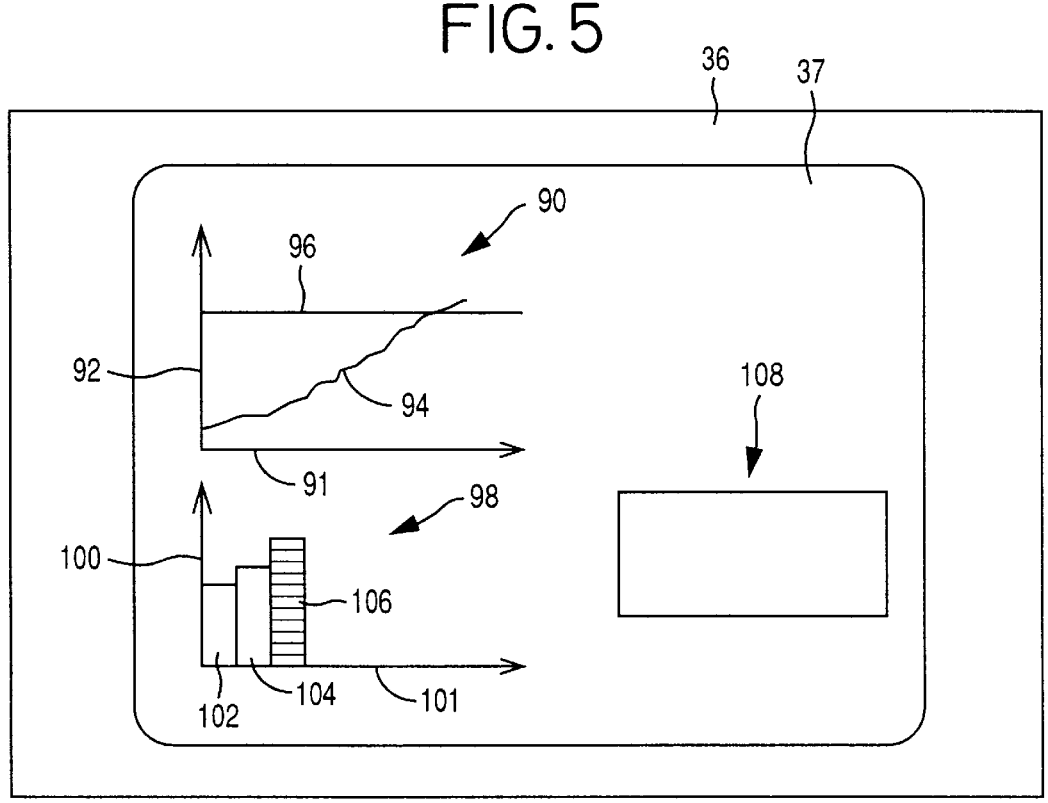
FIG. 5 is a view of an example of an image displayed on an image screen of a display device of the apparatus of FIG. 1.

The control device 28 is provided by a microcomputer including a central processing unit (CPU) 30, a read only memory (ROM) 32, a random access memory (RAM) 34, and an input and output (I/O) port (not shown). The CPU 30 processes input signals, including the signals SK, $SM_1$, by utilizing the temporary-storage function of the RAM 34, according to the control programs pre-stored in the ROM 32. In addition, the CPU 30 supplies drive signals via the I/O port to drive circuits (not shown) which are provided for the selector valve 16 and the air pump 18, respectively. Thus, the CPU 30 controls respective operations of the valve 16 and the pump 18. For example, when an oscillometric BP measurement using the cuff 10 is carried out to calibrate the BP measuring device 8, the CPU 30 controls the valve 16 and the pump 18 to increase quickly the cuff pressure up to a predetermined target value and subsequently decrease the cuff pressure at a low rate of 2 to 3 mmHg/sec. Based on the variation of the cuff pulse wave (CPW) represented by the pulse-wave signal $SM_1$ provided by the pulse-wave filter circuit 24 during the low-rate decreasing of the cuff pressure, the CPU 30 determines a systolic and a diastolic BP value of the patient, according to a known oscillometric BP measuring method. In addition, the CPU 30 commands a display device 36 to display, on an image screen 37 thereof, an image as shown in FIG. 5 (described in detail later).

Figure 2:
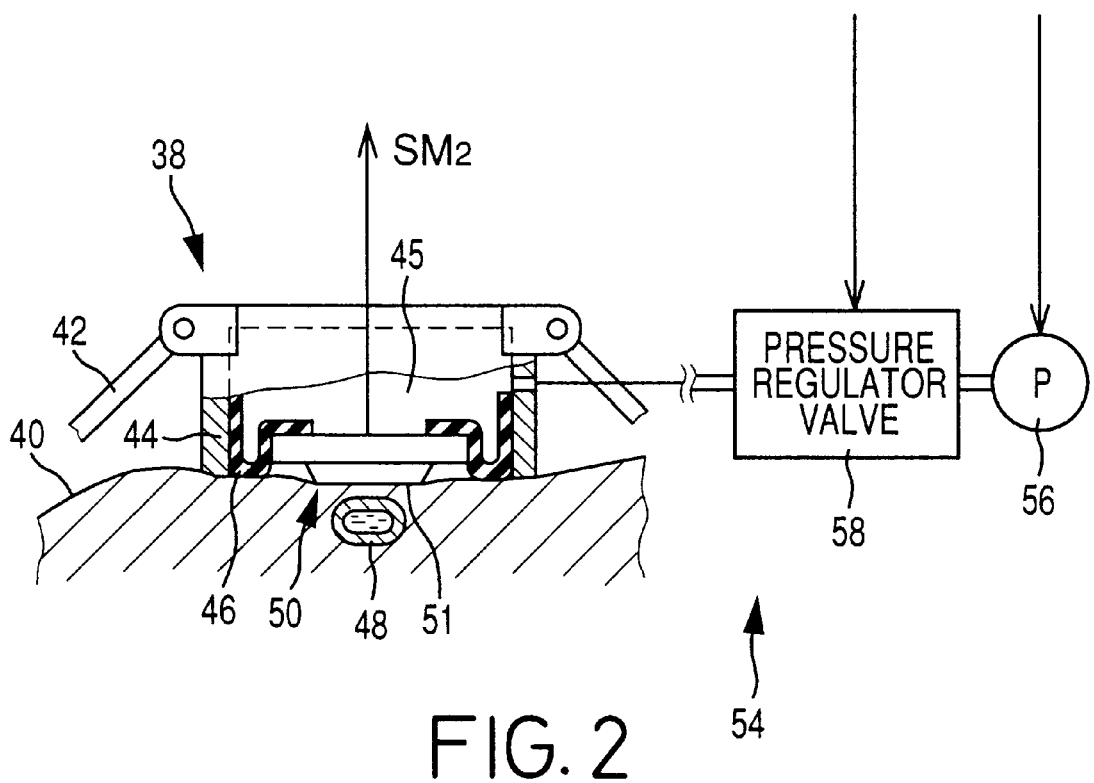
FIG. 2 is a view of a pressure pulse wave (PPW) sensor having a flat surface, and a flat-surface-pressing-force changing device, of the exercise apparatus of FIG. 1.

As shown in FIG. 2, a pressure-pulse-wave (PPW) sensor 38 includes a container-like sensor housing 44, and a pair of fastening bands 42 connected to the sensor housing 44. With the help of the fastening bands 42, the PPW sensor 38 is detachably attached to a wrist of the same arm 12 of the patient on which the cuff 10 is worn, or the other arm of the patient, such that an opening of the sensor housing 44 is opposed to a body surface or skin 40 of the patient. A press member 50 is secured via an elastic diaphragm 46 to inner surfaces of the sensor housing 44 such that the press member 50 is movable relative to the housing 44 and is advanceable through the opening of the housing 44 toward the body surface 40 of the patient. The sensor housing 44 and the diaphragm 46 cooperate with each other to define a pressure chamber 45, which is supplied with pressurized air from a second air pump 56 via a pressure regulator valve 58. Thus, the press member 50 is pressed on the body surface 40, that is, against a radial artery 48 with a pressing force, $P_{HD}$, corresponding to the air pressure in the pressure chamber 45. In the present embodiment, the pressing forces applied to the press member 50, i.e., applied to the body surface 40 are indicated in terms of pressure values (mmHg) in the pressure chamber 45. The sensor housing 44, the diaphragm 46, the pressure chamber 45, etc. cooperate with one another to provide a flat-surface pressing device which presses a flat surface 51 of the press member 50 against the radial artery 48 via the body surface or skin tissue 40. The second air pump 56 and the pressure regulator valve 58 cooperate with each other to provide a flat-surface-pressing-force changing device 54.

The press member 50 includes a semiconductor chip formed of a monocrystalline silicon with the flat surface 51, and a number of pressure-sensing semiconductor elements (not shown) which are arranged, in the flat surface 51, in an array at a regular interval of distance (about 0.2 mm), such that the array of pressure-sensing elements extends in the direction of width of the radial artery 48. When the press member 50 is pressed against the radial artery 48 via the body surface 40, each sensor element detects an oscillatory pressure wave, i.e., pressure pulse wave (PPW) which is produced from the radial artery 48 in synchronism with the heartbeat of the patient and is propagated via the body surface 40 to the press member 50. The PPW sensor 38 generates a PPW signal, $SM_2$, representing the detected PPW, and supplies the PPW signal $SM_2$ to the control device 28 via a third A/D converter 52.

The CPU 30 of the control device 28 processes the input signals, including the PPW signal $SM_2$, by utilizing the temporary-storage function of the RAM 34, according to the control programs pre-stored in the ROM 32, and supplies drive signals to drive circuits (not shown) which are provided for the second air pump 56 and the pressure regulator valve 58, respectively. Thus, the CPU 30 controls respective operations of the pump 56 and the valve 58 and thereby regulates the pressure of the pressure chamber 45 that is applied to the press member 50, i.e., the pressing force of the press member 50 applied to the radial artery 48 via the body surface or skin tissue 40.

The present exercise apparatus 4 further includes an input device 60, such as a keyboard, through which an operator such as a doctor or a nurse inputs various data including a target pressure-rate product, $PRP_M$, (described later). The thus input data are supplied to the control device 28. A clock circuit 62, connected to the control device 28, supplies a time of day to the control device 28 so that the control device 28 determines a time of day when a BP value is measured by the BP measuring device 8, or when a PPW is detected by the PPW sensor 38. In addition, the exercise apparatus 4 includes a card writing and reading device 64 into which a memory card 63 can be inserted. The memory card 63 is possessed by each individual patient, and functions as a memory which stores his or her name, age, sex, weight, pulse rate, prior exercise-function index value(s) (described later), test data obtained in prior exercise test(s), exercise-test date(s) and time(s) of day, etc. When the memory card 63 is inserted in the write/read device 64, the write/read device 64 reads those data from the card 63 so as to supply them to the control device 28, and simultaneously supplies a signal to command the control device 28 to start an exercise test, i.e., start an evaluation of the exercise function of the patient.

The ergometer 6 functions as an exercise-load applying device which applies an exercise load to the patient who undergoes an exercise test thereon. The ergometer 6 includes a pair of pedals 65, a chain 66, a rotary plate 67 which is operatively connected to the pedals 65 via the chain 66, and a generator 68 which is associated with the rotary plate 67 and which applies a controllable resistance to the rotation of the rotary member 67. The electric power produced by the generator 68 can be so controlled that the generator 68 functions as an electromagnetic brake which applies a controllable resistance to the rotary member 67. That is, when the resistance produced by the generator 68 is changed, the exercise load applied to the patient is changed. Thus, the generator 68 functions as an exercise-load changing device which changes the exercise load applied by the ergometer 6 to the patient who is doing exercise thereon. A wattmeter 69 (FIG. 3) measures an electric power, W, generated by the generator 68, that is, the work efficiency or power of the patient, and supplies data representing the measured power W to the control device 28.

When an exercise test is started on a patient, the CPU 30 determines an optimum pressing force, $P_{HDP}$, of the PPW sensor 38 applied to the radial artery 48, based on the PPW (i.e., PPW signal $SM_2$) obtained while the pressure of the pressure chamber 45 is slowly changed, and controls the pressure regulator valve 58 to maintain the pressure of the chamber 45 at the determined optimum pressing force $P_{HDP}$. In addition, the CPU 30 determines a relationship between BP values and PPW magnitudes $P_M$ (i.e., absolute voltage values of the PPW signal $SM_2$), based on systolic and diastolic BP values, $BP_{SYS}$, $BP_{DIA}$, measured using the cuff 10 according a known oscillometric BP measuring method, and a maximum and a minimum magnitude, $P_{Mmax}$, $P_{Mmin}$, of one heartbeat-synchronous pulse of the PPW detected by the PPW sensor 38 being pressed on the body surface 40 with the optimum pressing force $P_{HDP}$. According to the thus determined relationship, the CPU 30 estimates a systolic and a diastolic BP value (i.e., estimated BP values), $MBP_{SYS}$, $MBP_{DIA}$, of the patient, based on a maximum magnitude (i.e., upper-peak magnitude) $P_{Mmax}$ and a minimum magnitude (i.e., lower-peak magnitude) $P_{Mmin}$ of each of successive heartbeat-synchronous pulses of the PPW detected by the PPW sensor 38 being pressed on the body surface 40 with the optimum pressing force $P_{HDP}$. Subsequently, the CPU 30 controls the display 36 to successively display, for each heartbeat-synchronous pulse, the estimated BP values $MBP_{SYS}$, $MBP_{DIA}$, in digits, and continuously display the waveform of the PPW detected by the PPW sensor 38. This waveform represents the instantaneous estimated BP values MBP of the patient.

Figure 4:
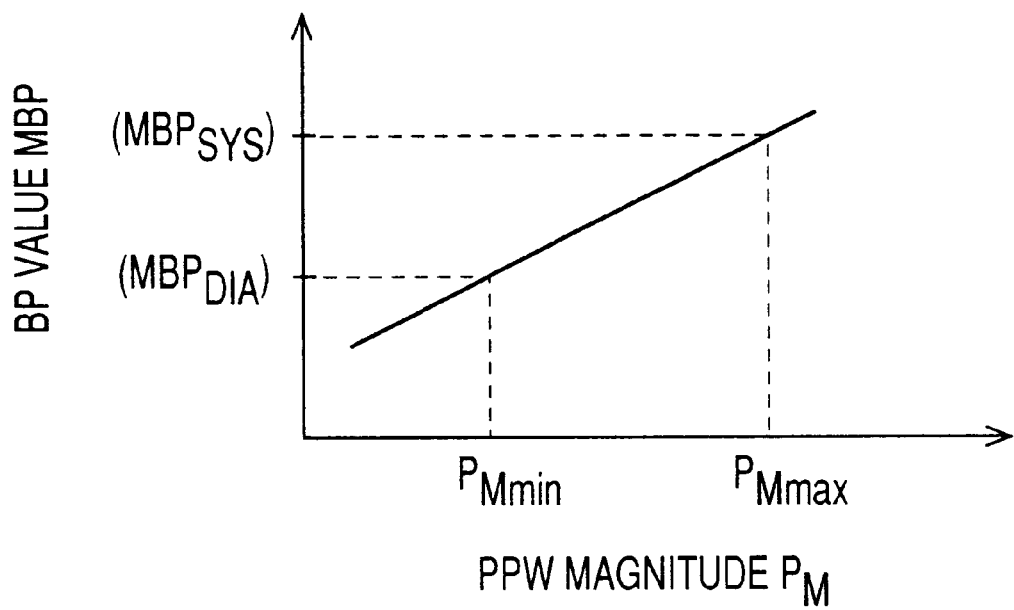
FIG. 4 is a graph showing a relationship between blood pressure and PPW magnitude determined by the control device of the apparatus of FIG. 1.

FIG. 4 shows an example of a relationship between BP values (estimated BP values MBP) and PPW magnitudes $P_M$ that is determined by the CPU 30. This relationship is expressed by the following linear function (1):

$$MBP = \alpha \bullet P_M + \beta \qquad \ldots (1)$$

where $\alpha$ is a constant corresponding to the slope of the linear function (1) and $\alpha$ is a constant corresponding to the intercept of the axis of ordinate indicative of estimated BP values MBP.

Figure 3:
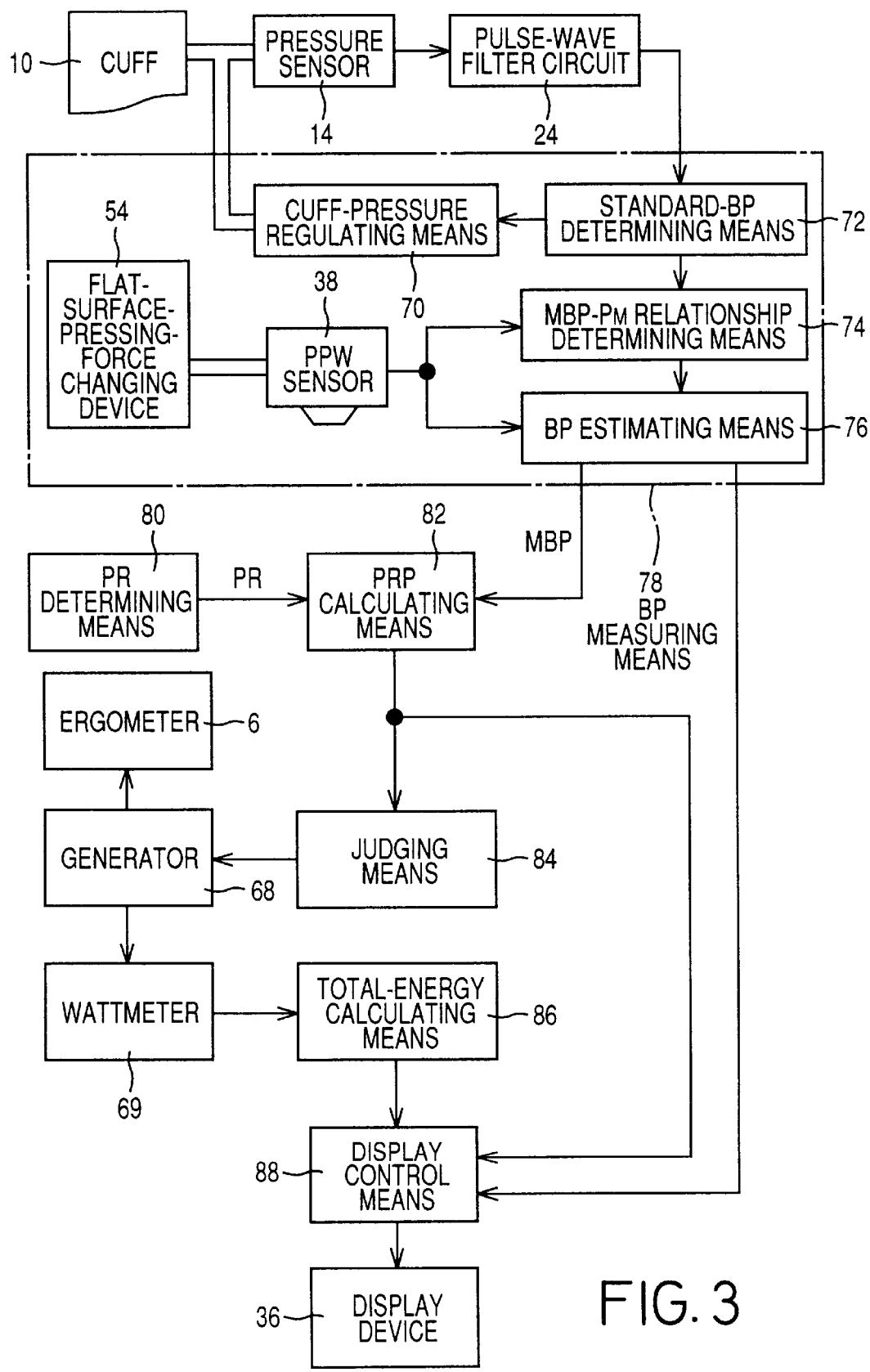
FIG. 3 is a block diagram for explaining various functions of a control device of the apparatus of FIG. 1.

FIG. 3 illustrates various functions of the control device 28 of the present exercise apparatus 4. The static-pressure filter circuit 22 cooperates with the control device 28 to provide a standard-BP determining means 72 which determines, according to an oscillometric BP measuring method (e.g., JIS T 1115; JIS is Japanese Industrial Standard), a systolic BP value $BP_{SYS}$, a mean BP value $BP_{MEAN}$, and a diastolic BP value $BP_{DIA}$ of a person based on the variation of respective amplitudes of heartbeat-synchronous pulses of the cuff pulse wave obtained while the pressure of the cuff 10 is slowly increased or decreased at the rate of 2 to 3 mmHg/sec. The cuff pulse wave (CPW) is represented by the pulse-wave signal $SM_1$ provided by the pulse-wave filter circuit 24. The thus determined BP values are standard BP values to be used for determining a $MBP$-$P_M$ relationship as shown in FIG. 4. The standard BP values are determined just after the operation of the present exercise apparatus 4 is started, or just before the application of an exercise load to the patient is started, and are displayed on the display device 36.

The PPW sensor 38 is preferably worn on the wrist of the other arm of the patient than the arm 12 on which the cuff 10 is worn, and detects the PPW produced from the radial artery 48 of the other arm. The flat-surface-pressing-force changing device 54 changes the pressing force of the flat-surface pressing device 44, 45, 46 applied to the flat surface 51 of the press member 50, so that a portion of the wall of the radial artery 48 is flattened under the flat surface 51 being pressed by the pressing device 44, 45, 46.

The control device 28 functions as a relationship determining means 74 which determines a $MBP$-$P_M$ relationship between estimated BP values MBP and PPW magnitudes $P_M$ that is expressed by the linear function (1) and is shown in FIG. 4, based on the magnitudes of PPW detected by the PPW sensor 38 and the standard BP values (at least two of the systolic, mean, and diastolic BP values $BP_{SYS}$, $BP_{MEAN}$, $BP_{DIA}$) determined by the standard-BP determining means 72.

The control device 28 also functions as a BP estimating means 76 which successively estimates, according to the $MBP$-$P_M$ relationship, a BP value MBP of the person based on a magnitude of each of heartbeat-synchronous pulses of the PPW detected by the PPW sensor 38. The estimated BP values MBP are successively displayed on the display device 36. The estimated BP values MBP may comprise an estimated systolic BP value corresponding to the maximum magnitude (i.e., upper-peak magnitude) of each heartbeat-synchronous pulse of the PPW signal $SM_2$, an estimated diastolic BP value corresponding to the minimum magnitude (i.e., lower-peak magnitude) of the same pulse of the PPW signal $SM_2$, and an estimated mean BP value corresponding to the mean magnitude of the same pulse of the PPW signal $SM_2$. The mean magnitude of each pulse of the PPW signal $SM_2$ may be defined as the height or magnitude of the center of gravity of an area defined by the waveform of that pulse and a base line passing through the lower-peak point (i.e., minimum magnitude) of that pulse.

The selector valve 16 and the first air pump 18 cooperate with the control device 28 to provide a cuff-pressure regulating device 70 which regulates the pressure of the cuff 10 (i.e., cuff pressure), which is detected by the pressure sensor 14 when an oscillometric BP measurement using the cuff 10 is carried out by the standard-BP determining means 72. The cuff-pressure regulating device 70 changes the cuff pressure according to a well-known procedure, so that the standard-BP determining means 72 determines standard BP values of the patient using the cuff 10 just before the application of the exercise load to the patient is started and so that the relationship determining means 74 updates the $MBP$-$P_M$ relationship based on the standard BP values newly measured using the cuff 10. For example, the regulating device 70 increases the cuff pressure up to a target value, e.g., 180 mmHg, which is higher than an estimated systolic BP value of the patient and subsequently decreases the cuff pressure slowly at the rate of 2 to 3 mmHg/sec during a measurement period in which standard BP values of the patient are determined by the standard-BP determining means 72 according to a well-known oscillometric BP determining algorithm. After the standard-BP measuring operation, the regulating device 70 quickly deflates the cuff 10 down to the atmospheric pressure.

In the present embodiment, the cuff-pressure regulating device 70, the standard-BP determining means 72, the PPW sensor 38, the flat-surface-pressing-force changing device 54, the relationship determining means 74, and the BP estimating means 76 cooperate with one another to provide a blood-pressure measuring means 78 which successively and non-invasively measures a blood pressure MBP of the patient in synchronism with the heartbeat of the patient.

The control device 28 also functions as a pulse-rate (PR) determining means 80 which successively measures a pulse rate, PR, of the patient in synchronism with the heartbeat of the patient. For example, the PR determining means 80 determines a pulse rate PR from the time difference between each pair of successive heartbeat-synchronous pulses of the PPW signal $SM_2$ supplied from the PPW sensor 38.

The control device 28 also functions as a PRP calculating means 82 which successively calculates a product, PRP, of a pulse rate PR and a blood pressure MBP (PRP=PR×MBP) in synchronism with the heartbeat of the patient.

The control device 28 also functions as a judging means 84 which judges whether the pressure-rate products PRP successively calculated by the PRP calculating means 82 have increased up to the target value $PRP_M$. When the judging means 84 makes a positive judgment, the exercise-load changing device (generator) 68 zeroes the exercise load applied to the patient by the exercise-load applying device (ergometer) 6.

The control device 28 additionally functions as a a total-energy calculating means 86 which calculates, based on the output of the wattmeter 69, a total energy, WH (watt-hour), which is produced by the patient after the application of the exercise load to him or her is started and before it is judged by the judging means 84 that the pressure-rate products PRP successively calculated by the PRP calculating means 82 have increased up to the target value $PRP_M$.

The control device 28 also functions as a display control means 88 which controls the display device 36 to display, in a first display section 98 on the image screen 37, an evaluation value of the exercise function of the patient, based on the total energy WH itself calculated by the total-energy calculating means 86, as shown in FIG. 5. In the figure, an analogue bar 106 representing the total energy measured in the current exercise test is displayed as an evaluation value indicated by an axis of ordinate 100, in addition to one or more analogue bars 102, 104 representing the total energy value or values WH measured in the prior exercise test or tests, along an axis of abscissa 101 indicative of time. In addition, the display device 36 displays, in a second display section 90 on the screen 37, an orthogonal coordinate system defined by an axis of abscissa 91 indicative of time and an axis of ordinate 92 indicative of pressure-rate product PRP. A straight line 96 represents the target value $PRP_M$, and a curve 94 represents a time-wise change of the pressure-rate products PRP successively calculated by the PRP calculating means 82. A digital value of the total energy WH measured in the current exercise test is displayed in a third display section 108 on the screen 37.

Figure 6:
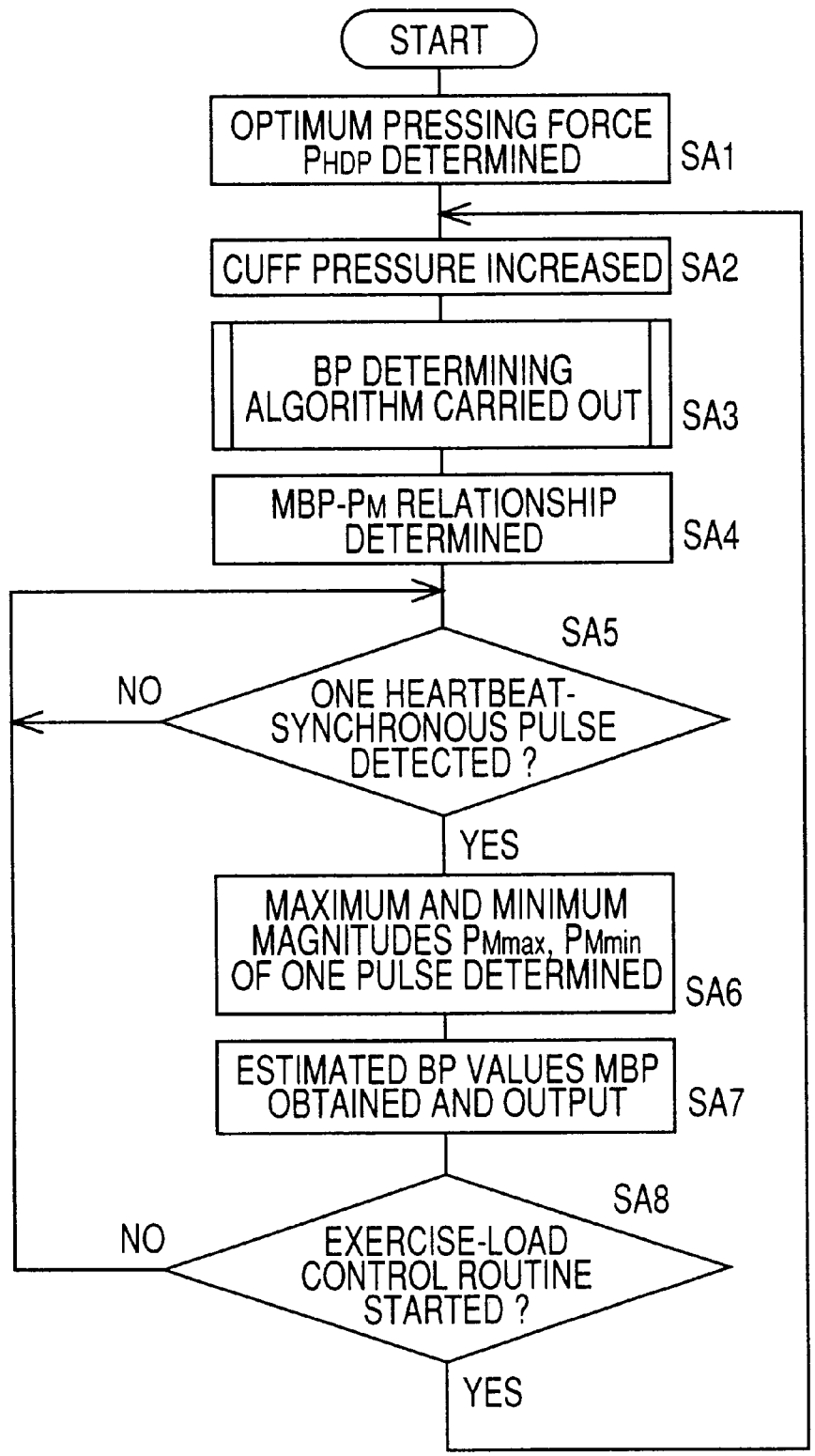
FIG. 6 is a flow chart representing a blood-pressure-measurement control routine according to which the control device of the apparatus of FIG. 1 operates for successively measuring a blood pressure of a person in synchronism with the heartbeat of the person.
Figure 7:
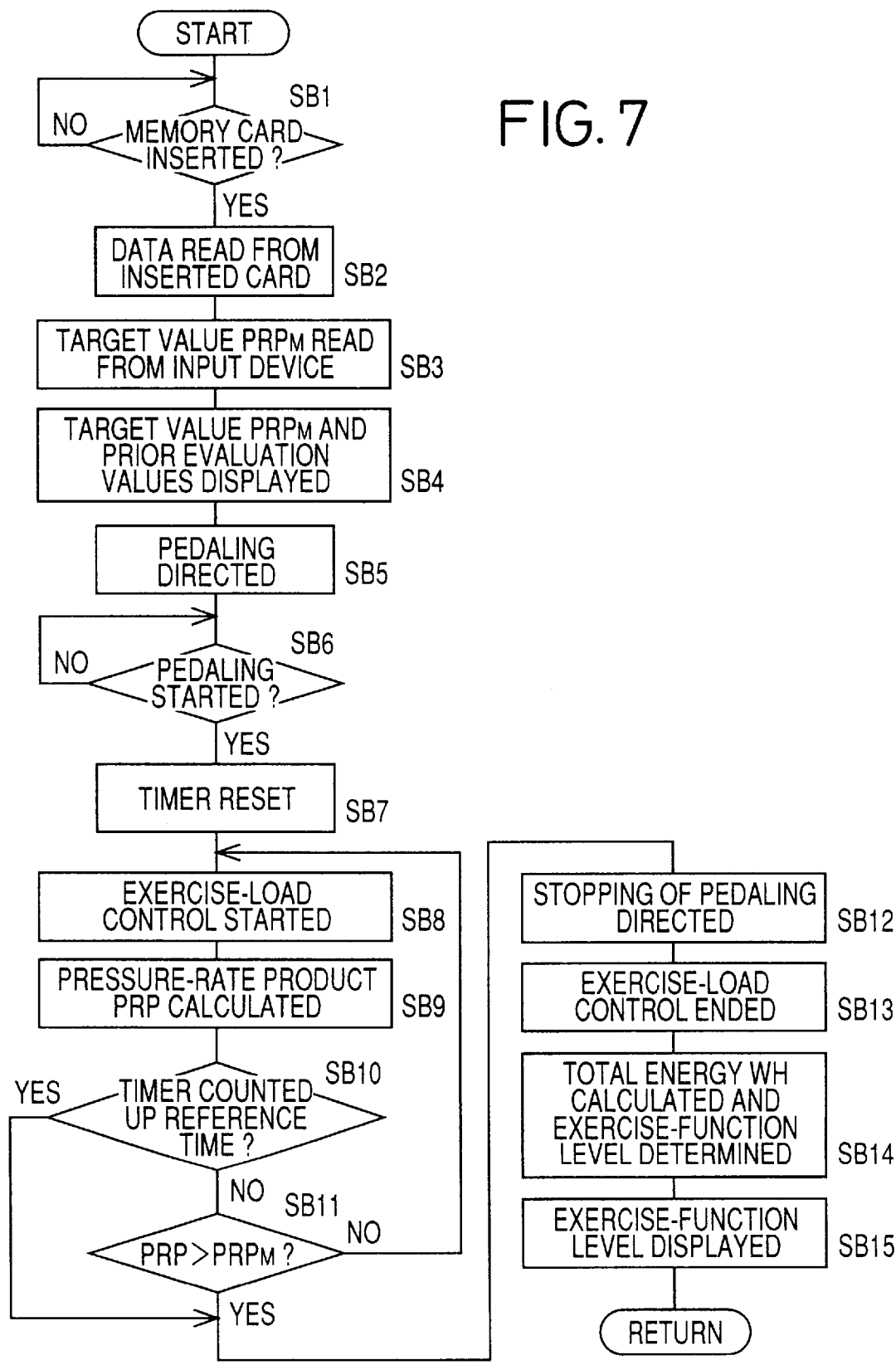
FIG. 7 is a flow chart representing an exercise-load control routine according to which the control device of the apparatus of FIG. 1 operates for changing an exercise load applied to the person by an ergometer.

Next, there will be described the operation of the exercise apparatus 4 constructed as described above, by reference to the flow charts of FIGS. 6 and 7 representing the control programs pre-stored in the ROM 32. More specifically, the flow chart of FIG. 6 represents a successive BP measurement routine in which an estimated BP value MBP is obtained from each of heartbeat-synchronous pulses of the PPW signal $SM_2$, and the flow chart of FIG. 7 represents an exercise-load control routine in which the exercise load applied to a patient by the ergometer 6 is controlled so that the pressure-rate products PRP increase up to the target value $PRP_M$ and the exercise function of the patient is evaluated based on the total energy WH produced by the patient until then.

First, at Step SA1, the CPU 30 of the control device 28 controls the second air pump 56 and the pressure regulator valve 58 to increase slowly the pressure of the pressure chamber 45, and determines, as an optimum pressing force $P_{HDP}$, a pressure of the chamber 45 when the PPW sensor 38 detects a maximum pulse having the greatest amplitude of the respective amplitudes of all the pulses detected thereby during the slow increasing of the pressure of the chamber 45. Subsequently, the CPU 30 holds the pressure of the chamber 45 at the thus determined optimum pressing force $P_{HDP}$. Thus, the optimum pressing force $P_{HDP}$ is applied to the PPW sensor 38 to flatten partially the wall of the radial artery 48 via the body surface 40.

Next, the control of the CPU 30 proceeds with Step SA2 to start increasing the pressure of the cuff 10 for measuring standard BP values of the patient. Step SA2 corresponds to the cuff-pressure regulating means 70. Step SA2 is followed by Step SA3 to carry out a known oscillometric BP determining algorithm. More specifically described, the selector valve 16 is switched to the first state and the first air pump 18 is operated, so that the cuff pressure continues to increase up to a target pressure (e.g., 180 mmHg) higher than an estimated systolic BP value of the patient. Subsequently, the air pump 18 is stopped and the selector valve 16 is switched to the second state, so that the cuff pressure decreases at a predetermined low rate (e.g., about 3 mmHg/sec). Based on the variation of respective amplitudes of heartbeat-synchronous pulses of the cuff-pulse-wave (CPW) signal $SM_1$ obtained during this slow decreasing of the cuff pressure, the CPU 30 determines a systolic, a mean, and a diastolic BP value $BP_{SYS}$, $BP_{MEAN}$, $BP_{DIA}$ of the patient according to the oscillometric BP determining algorithm. More specifically, the CPU 30 determines, as the systolic BP value $BP_{SYS}$, a cuff pressure at the time when the pulse amplitudes significantly largely increase, determines, as the diastolic BP value $BP_{DIA}$, a cuff pressure at the time when the pulse amplitudes significantly largely decrease, and determines, as the mean BP value $BP_{MEAN}$, a cuff pressure at the time when the pulse amplitudes become maximum. In addition, the CPU 30 determines a pulse rate PR of the patient based on the time difference or interval between respective upper peaks of two successive heartbeat-synchronous pulses of the CPW signal $SM_1$. The thus measured standard BP values and pulse rate PR are stored in the RAM 34 and displayed on the display device 36. Then, the selector valve 16 is switched to the third state, so that the cuff pressure is quickly decreased to the atmospheric pressure. Step SA3 corresponds to the standard-BP determining means 72.

Subsequently, the control of the CPU 30 goes to Step SA4 to determine a relationship between estimated BP value MBP and magnitude $P_M$ of pressure pulse wave (i.e., voltage of the pressure-pulse-wave (PPW) signal $SM_2$) as shown in FIG. 4. More specifically described, the CPU 30 newly reads in one heartbeat-synchronous pulse of the PPW signal $SM_2$ supplied from the PPW sensor 38, determines a maximum and a minimum magnitude $P_{Mmax}$, $P_{Mmin}$ of the one pulse, and determines the previously-indicated linear function (1) based on the systolic and diastolic BP values $BP_{SYS}$, $BP_{DIA}$ of the patient measured at Step SA3 and the thus determined maximum and minimum magnitudes $P_{Mmax}$, $P_{Mmin}$ of the one pulse of the PPW signal $SM_2$. Step SA4 corresponds to the relationship determining means 74.

After the MBP-$P_M$ relationship shown in FIG. 4 is determined at Step SA4, the control of the CPU 30 goes to Step S5 to judge whether the CPU 30 has read in one heartbeat-synchronous pulse of the PPW signal $SM_2$ supplied from the PPW sensor 38 being pressed at the optimum pressing force $P_{HDP}$. If a negative judgment is made at Step SA5, the CPU 30 waits for detecting one pulse of the PPW signal $SM_2$. Meanwhile, if a positive judgment is made at Step SA5, the control of the CPU 30 goes to Step SA6 to determine a maximum (upper-peak) magnitude $P_{Mmax}$ and a minimum (lower-peak) magnitude $P_{Mmin}$ of the one pulse of the PPW signal $SM_2$. Step SA6 is followed by Step SA7 to estimate a systolic and a diastolic BP value $MBP_{SYS}$, $MBP_{DIA}$ (i.e., estimated BP values) of the patient, based on the maximum and minimum magnitudes $P_{Mmax}$, $P_{Mmin}$ of the one pulse of the PPW signal $SM_2$ determined at Step SA6, according to the MBP-$P_M$ relationship determined at Step SA4. In addition, the CPU 30 determines an actual pulse rate PR from the time interval between each pair of successive heartbeat-synchronous pulses of the PPW signal $SM_2$. The CPU 30 controls the display device 36 to display, on the image screen 37, not only the estimated BP values MBP and the determined pulse rate PR but also the waveform of the one pulse that is continuous with the respective waveforms of the previous pulses. Steps SA6 and SA7 correspond to the BP estimating means 76. Step SA7 also corresponds to the PR determining means 80.

Subsequently, the control of the CPU 30 goes to Step SA8 to judge whether the exercise-load control routine of FIG. 7 should be started. When the memory card 63 is inserted in the card write/read device 64, or when the rotation of the pedals 65 of the ergometer 6 is started by the patient, a positive judgment is made at Step SA8. If a negative judgment is made at Step SA8, the control of the CPU 30 goes back to Step SA5 and the following steps, i.e., BP monitor routine in which estimated systolic and diastolic BP values $MBP_{SYS}$, $MBP_{DIA}$ are obtained for each heartbeat-synchronous pulse of the PPW signal $SM_2$ and are displayed on the display device 36. On the other hand, if a positive judgment is made at Step SA8, the control goes back to Step SA2 and the following steps to update the $MBP-P_M$ relationship, i.e., determine a new $MBP-P_M$ relationship. That is, just before the control of the CPU 30 enters the exercise-load control routine of FIG. 7, new standard BP values are measured at Step SA3, and a new $MBP-P_M$ relationship is determined based on the new standard BP values at Step SA4.

While estimated systolic and diastolic BP values $MBP_{SYS}$, $MBP_{DIA}$ are obtained for each of successive heartbeat-synchronous pulses of the PPW signal $SM_2$, according to the newly determined or updated $MBP-P_M$ relationship, the control of the CPU 30 enters the exercise-load control routine of FIG. 7. First, at Step SB1, the CPU 30 judges whether a memory card 63 has been inserted in the card write/read device 64. If a negative judgment is made at Step SB1, Step SB1 is repeated. On the other hand, if a positive judgment is made at Step SB1, the control of the CPU 30 goes to Step SB2 to read in the data recorded on the memory card 63, and then goes to Step SB3 to read the target value $PRP_M$ from the input device 60. The input device 60 temporarily stores the target value $PRP_M$ input by the operator. Otherwise, the control device 28 or the CPU 30 may be modified to determine automatically a target value $PRP_M$, according to a plurality of sorts of relationships (i.e., data maps), based on the age, sex, weight, pulse rate, and prior exercise-function evaluation value or values read from the card 63. The target value $PRP_M$ may be determined as the product of a systolic BP value measured from the patient at rest and a pulse rate greater by a predetermined ratio of 50 to 100% than a pulse rate measured from the patient at rest. The CPU 30 automatically determines this ratio based on the data including the age, sex, weight, pulse rate, and prior exercise-function evaluation values of the patient.

Step SB3 is followed by Step SB4 to control the display device 36 to display, on the image screen 37, a straight line 90 representing the target value $PRP_M$, parallel to the time axis 91 in the second display section 90, and one or more bars 102, 104 representing one or more prior exercise-function evaluation values obtained in one or more prior exercise tests and recorded on the memory card 63, parallel to the exercise-function-evaluation-value axis 100 in the first display section 98.

Subsequently, the control of the CPU 30 goes to Step SB5 to issue, to the patient, a message "PLEASE PEDAL ERGOMETER TILL YOU ARE DIRECTED TO STOP" as a voice or an indication on the display device 36. Step SB5 is followed by Step SB6 to judge whether the patient has started pedaling the ergometer 6. If a negative judgment is made at Step SB6, Step SB6 is repeated. On the other hand, if a positive judgment is made at Step SB6, the control of the CPU 30 goes to Step SB7.

At Step SB7, the CPU 30 resets the content of a timer incorporated in the microcomputer, to zero, and command the timer to restart measuring or counting time. Step SB7 is followed by Step SB8 to control the generator 68 in such a manner that the ergometer 6 applies an exercise load to the patient according to a straight or curved line representing a predetermined exercise-load value or a predetermined exercise-load pattern. Subsequently, at Step SB9, the CPU 30 reads in the estimated systolic BP value $MBP_{SYS}$ and actual pulse rate PR obtained for one heartbeat-synchronous pulse of the PPW signal $SM_2$, and calculates a pressure-rate product PRP by multiplying the estimated systolic BP value $MBP_{SYS}$ by the actual pulse rate PR. Step SB9 corresponds to the PRP calculating means 82. As Step SB9 is repeated, the curve 94 representing the pressure-rate products PRP, i.e., exercise load internally applied to the patient, grows or extends little by little on the image screen 37. FIG. 5 shows the state in which the products PRP have just increased up to, and become equal to, the target value $PRP_M$.

Subsequently, the control of the CPU 30 goes to Step SB10 to judge whether the timer has measured or counted up a predetermined reference time. If a negative judgment is made at Step SB10, the control goes to Step SB11. On the other hand, if a positive judgment is made at Step SB10, the control goes to Step SB12. If the products PRP do not reach the target value $PRP_M$ within the reference time, i.e., if the exercise function of the patient is not evaluated within that time, then the CPU 30 judges that an abnormality has occurred because, e.g., the applied exercise load is too low or light to the patient. The reference time is appropriately predetermined to satisfy this. In the latter case, the control of the CPU 30 goes to Step SB12 to terminate the current control cycle in accordance with the control routine of FIG. 7.

At Step SB11, the CPU 30 judges whether the products PRP have increased up to the target value $PRP_M$ within the reference time. Step S11 corresponds to the judging means 84. If a negative judgment is made at Step SB11, the control of the CPU 30 goes back to Step SB8 and the following steps. On the other hand, if a positive judgment is made at Step SB11, the control of the CPU 30 goes to Step SB12 to control the generator 8 to zero the resistance to the rotation of the rotary member 67, i.e., exercise load applied to the patient and then issue, to the patient, a message "PLEASE STOP PEDALING ERGOMETER" as a voice or an indication on the display device 36. According to this message, the patient stops rotating the pedals 65 of the ergometer 6. Step SB12 is followed by Step SB13 to terminate the control of the exercise load applied by the ergometer 6.

Subsequently, at Step SB14, the CPU 30 calculates, based on the data supplied from the wattmeter 69, a total electric power (watt●hour), i.e., total energy WH produced by the generator 68 of the ergometer 6 during the exercise-load control operation according to the routine of FIG. 7. The CPU 30 determines the thus measured total energy WH itself as an evaluation value indicative of the exercise function of the patient, or selects one of a predetermined number (e.g., 5) of exercise-function levels which corresponds to the measured total energy WH. Step SB14 corresponds to the total-energy calculating means 86.

Step SB14 is followed by Step SB15 to display a bar 106 representing either the measured total energy WH itself or the selected exercise-function level in the first section 98, and digits representing the same in the third section 108, on the image screen 37 of the display device 36. Step SB15 corresponds to the display control means 88. In addition, the exercise-function evaluation value or the exercise-function level, and the test data obtained in the current exercise test are recorded on the memory card 63 by the card write/read device 64. In the case where a positive judgment is made at Step SB10, Step SB14 is skipped and, at Step SB15, the CPU 30 controls the display device 36 to indicate, in the screen 37, that the reference time has passed before the products PRP reach the target value $PRP_M$.

As is apparent from the foregoing description, the present exercise apparatus 4 determines the total energy WH produced by the generator 68 of the ergometer 6, i.e., total energy produced by the patient before the pressure-rate products PRP representing the patient's physical response to the exercise test increase up to the target value $PRP_M$, and displays, on the display device 38, the exercise-function evaluation value 106, 108 based on the determined total energy WH. Thus, the present apparatus 4 automatically evaluates the exercise function of the patient.

In the illustrated embodiment, at Step SB15, the control device 28 or the display control means 88 controls the display 36 to display, in the first section 98 of the screen 37, the new bar 106 representing the current evaluation value in addition to the old bars 102, 104 representing the prior evaluation values. Thus, a doctor or a nurse can recognize a significant change of the exercise function of the patient by comparing the new bar 106 with the old bars 102, 104.

Also in the illustrated embodiment, the display 36 displays the curve 94 representing the time-wise change of the pressure-rate products PRP, while the patient undergoes the exercise test. Since the curve 94 grows or extends little by little as the products PRP increase toward the target value $PRP_M$, the patient is encouraged to continue his or her monotonous pedaling work in the exercise test. However, the first and/or second display sections 98, 90 may be omitted since they are not essential to evaluate the exercise function of the patient.

In the present exercise apparatus 4, at Steps SA1 to SA8, the BP measuring device 8 or the BP measuring means 78 successively and non-invasively measures or estimates the BP values MBP in synchronism with the heartbeat of the patient, and at Step SB9 the PRP calculating means 82 successively calculates the pressure-rate products PRP in synchronism with the heartbeat of the patient. Thus, at Step SB11, the control device 28 or the judging means 84 can judge, without delay, whether the actual pressure-rate 3products PRP have increased up to the target value $PRP_M$. Thus, the present apparatus 4 can evaluate the exercise function of the patient with high accuracy.

In the illustrated embodiment, the BP measuring means 78 includes the cuff-pressure regulating device 70 which changes the pressing pressure of the cuff 10 applied to the brachial artery of the upper arm 12, at a predetermined rate; the standard-BP determining means 72 which determines one or more standard BP values of the patient based on the variation of the heartbeat-synchronous wave $SM_1$ obtained while the pressing force of the cuff 10 is changed; the PPW sensor 38 adapted to be pressed against the radial artery 48 of the patient via the skin tissue 40 above the artery 48 so as to detect one or more magnitudes of the PPW $SM_2$ produced from the artery 48 in synchronism with the heartbeat of the patient; the relationship determining means 74 which determines a relationship between blood pressure and PPW magnitude, based on the standard BP value(s) determined by the standard-BP determining means 72 and the magnitude(s) of the PPW $SM_2$ detected by the PPW sensor 38; and the BP estimating means 76 which successively estimates a BP value of the patient, based on a magnitude of each of a plurality of heartbeat-synchronous pulses of the actual PPW $SM_2$ detected by the PPW sensor 38, according to the relationship determined by the relationship determining means 74. A standard BP value or values determined by the standard-BP determining means 72 are highly reliable, and a relationship between BP value and PPW magnitude is determined based on the highly reliable standard BP value or values and the magnitude or magnitudes of the PPW $SM_2$ detected by the PPW sensor 38. The BP estimating means 76 successively estimates a BP value MBP of the patient, based on a magnitude of each of heartbeat-synchronous pulses of the actual PPW $SM_2$ detected by the PPW sensor 38, according to the thus determined relationship between BP value and PPW magnitude. Thus, the estimated BP values MBP, successively obtained in synchronism with the heartbeat of the patient, enjoy a considerably high accuracy.

In the illustrated embodiment, the cuff 10 is used as a pressing device which presses a body portion 12 of a person as a subject, and the cuff-pressure regulating device 70 is used as a cuff-pressure changing device which changes the air pressure in the cuff 10. The standard-BP determining means 72 determines a standard BP value or values of the person based on the variation of respective amplitudes of heartbeat-synchronous pulses of the CPW $SM_1$ that is a pressure oscillation produced in the cuff 10 while the cuff pressure is changed. This is a so-called oscillometric BP measuring method that has been proved to be highly reliable. Since an $MBP-P_M$ relationship is determined based on the thus determined standard BP value or values, the BP values MBP estimated according to the $MBP-P_M$ relationship enjoy a high reliability.

In the illustrated embodiment, the PPW sensor 38 includes the press member 50 having the flat surface 51 adapted to be pressed against the radial artery 48 of the patient via the skin tissue 40, and the pressure sensing elements (not shown) are arranged in an array in the flat surface 51. The flat-surface pressing device 44, 45, 46 presses the flat surface 51 against the radial artery 48 via the skin tissue 40, and the BP measuring means 78 includes the flat-surface-pressing-force changing device 54 which controls the flat-surface pressing device to press the flat surface 51 against the artery 48 via the skin 40 such that a portion of the wall of the artery 48 is flattened under the flat surface 51 and the skin 40. In this case, since a portion of the wall of the artery 48 is flattened under the flat surface 51 in which the pressure sensing elements are provided, the PPW detected by each of the pressure sensing elements is least influenced by the tensile force of the arterial wall. Thus, the PPW detected by the PPW sensor 38 enjoys a high accuracy and accordingly the BP-PPW relationship determined based on the thus detected PPW enjoys a high accuracy. In addition, the estimated BP values MBP and the calculated pressure-rate products PRP also enjoy a high accuracy. The PPW sensor 38 may be modified to be pressed against a dorsal pedal artery of an ankle of a leg of a person.

In the illustrated embodiment, the standard-BP determining means 72 determines one or more standard BP values of the patient, before the application of the exercise load to the patient is started, and the relationship determining means 74 determines an $MBP-P_M$ relationship between BP value and PPW magnitude, based on the standard BP value or values determined by the standard-BP determining means 72 and the magnitude of the PPW $SM_2$ detected by the PPW sensor 38 before the commencement of the exercise-load control operation. In the case where the MBP-$P_M$ relationship is determined just before the commencement of the exercise-load control operation, BP values of the patient are estimated by the BP estimating means 76 with higher accuracy according to the new MBP-$P_M$ relationship and accordingly pressure-rate products PRP of the patient are calculated with higher accuracy. Those accurate products PRP are utilized for evaluating the exercise function of the patient.

In the illustrated embodiment, at Step SB11, the control device 28 or the judging means 84 judges whether the pressure-rate products PRP calculated by the PRP calculating means 82 have increased up to the target value $PRP_M$. If the judging means 84 makes a positive judgment, then the control device 28 controls the ergometer 6 or the generator 68 to zero the exercise load applied to the patient. That is, immediately after the pressure-rate products PRP have increased up to the target value $PRP_M$, the exercise load applied to the patient is zeroed. Thus, only the least possible burden is put on the patient for evaluating his or her exercise function.

The present exercise apparatus 4 includes, as the exercise-load changing device, the generator 68 associated with the rotary member 67 that is rotated by the patient through the pedals 65. The control device 28 or the total-energy calculating means 86 calculates the total energy WH produced by the generator 68, as the total energy produced by the patient. Thus, both the application of the exercise load to the patient by the ergometer 6 and the measurement of the total energy produced by the patient are carried out by using the generator 68. Thus, the present apparatus 4 enjoys a simple construction.

Figure 8:
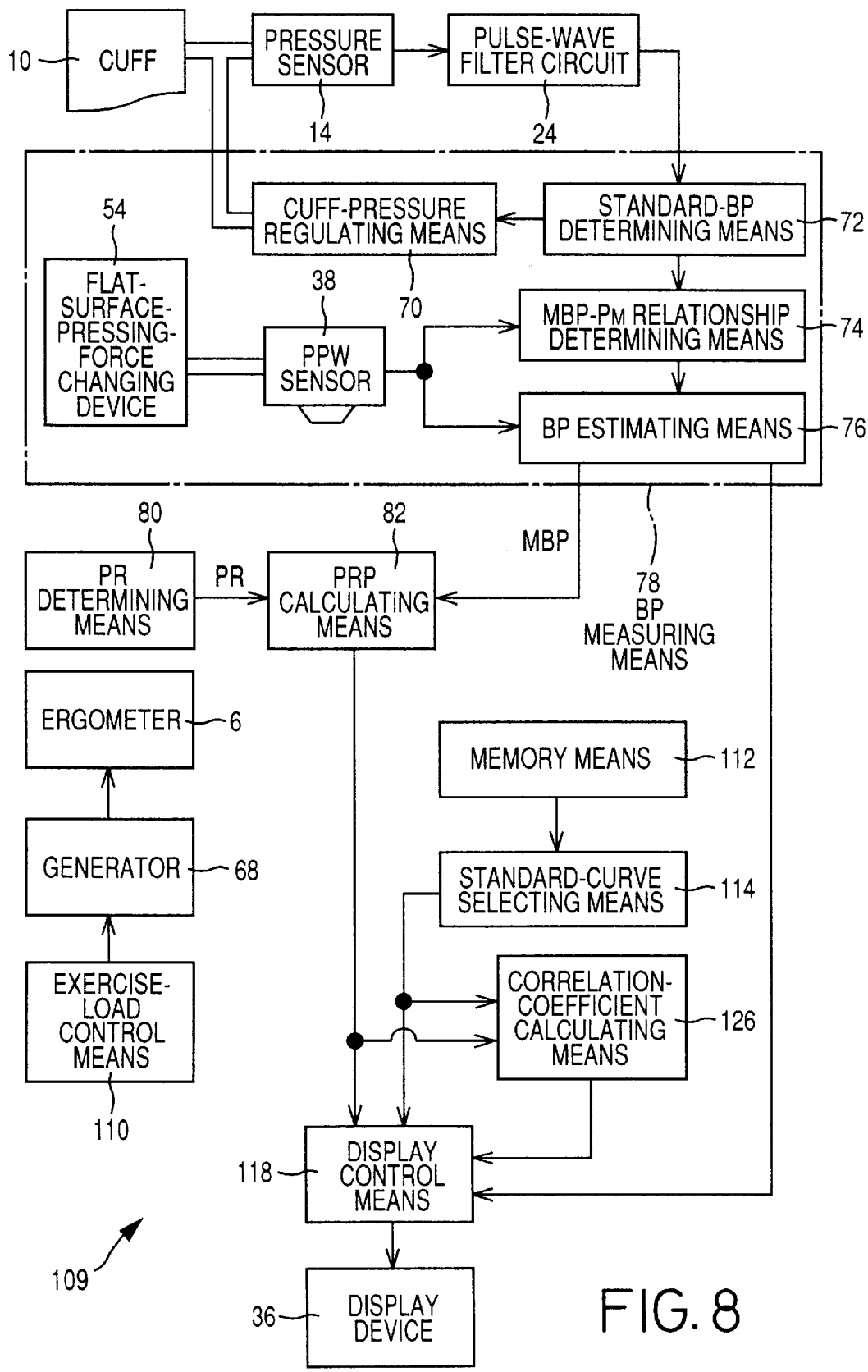
FIG. 8 is a block diagram corresponding to FIG. 3, for explaining various functions of a control device of another exercise apparatus as a second embodiment of the present invention.

Referring next to FIGS. 8 to 11, there will be described a second embodiment of the present invention. The second embodiment also relates to an exercise apparatus having the same hardware construction as that of the exercise apparatus 4 shown in FIG. 1, except that the second exercise apparatus includes a control device 109 shown in FIG. 8 in place of the control device 28 shown in FIG. 3. The control device 109 of FIG. 8 is different from the control device 28 of FIG. 3 in that the control device 109 functions as an exercise-load control means 110, a memory means 112, a standard-curve selecting means 114, a correlation-coefficient calculating means 126, and a display control means 118. The same reference numerals as used in the first embodiment are used to designate the corresponding elements or means of the second embodiment and the description thereof is omitted from the following description, which relates to only the differences between the first and second embodiments.

The exercise-load control means 110 controls a generator 68 functioning as an exercise-load changing device, to apply a changeable resistance to the rotation of a rotary member 67, so that a predetermined exercise load is applied to a patient for evaluating his or her exercise function. More specifically described, the control means 110 controls the generator 68 of an ergometer 6 functioning as an exercise-load applying device, in such a manner that during a start period, A, (FIG. 5) the ergometer 6 applies exercise load to the patient, thereby letting him or her to rotate easily pedals 65 of the ergometer 6; during an intermediate period, B, the ergometer 6 applies an exercise load which increases as time elapses at a predetermined rate according to a predetermined exercise-load pattern; and during an end period, C, the ergometer 6 applies no exercise load.

The memory means 112 may be provided by a ROM 32 of the control device 109. The memory means 112 stores a plurality of standard curves each of which represents a standard time-wise change of pressure-rate products PRP. Each standard curve is so predetermined as to correspond to a specific age, sex, weight, and exercise-function level.

The standard-curve selecting means 114 selects one 116 (FIG. 5) of the different standard curves pre-stored in the memory means 112, based on the age, sex, weight, and exercise-function level of an individual patient which are read from a memory card 63 being inserted in a card writing and reading device 64.

The display control means 118 controls a display device 36 to display, little by little on an image screen 37, a current actual curve 120 representing an actual time-wise change of the pressure-rate products PRP successively calculated by a PRP calculating means 82, in addition to the standard curve 116 selected by the standard-curve selecting means 114 and a prior actual curve 121 obtained in a prior exercise-function evaluation, in an orthogonal coordinate system defined by an axis of abscissa 122 indicative of time and an axis of ordinate 124 indicative of pressure-rate product PRP, so that an observer such as a doctor or a nurse can compare the three curves 116, 120, 121 with one another.

Figure 9:
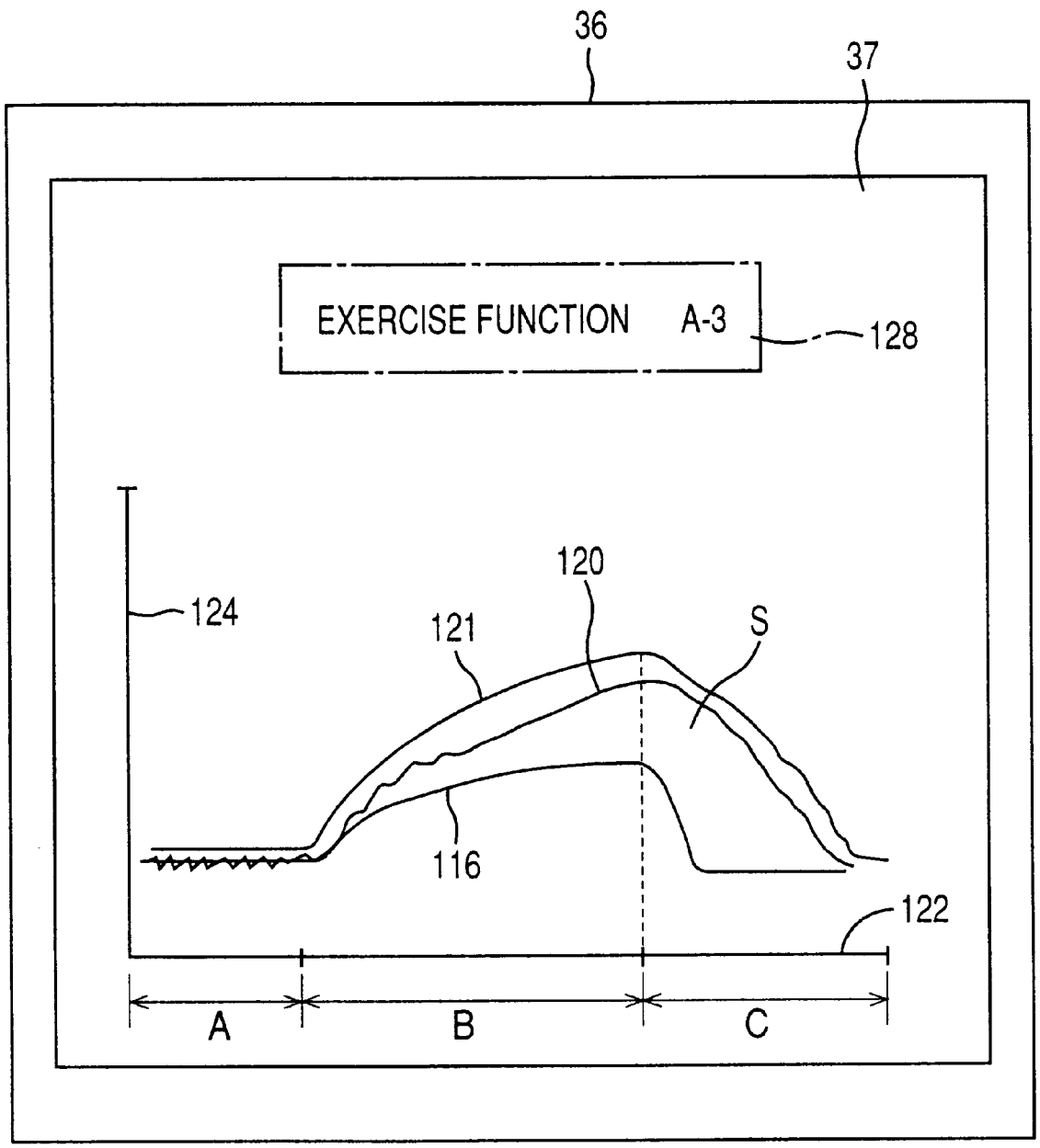
FIG. 9 is a view corresponding to FIG. 5, showing an example of an image displayed on an image screen of a display device of the apparatus of FIG. 8.
Figure 10:
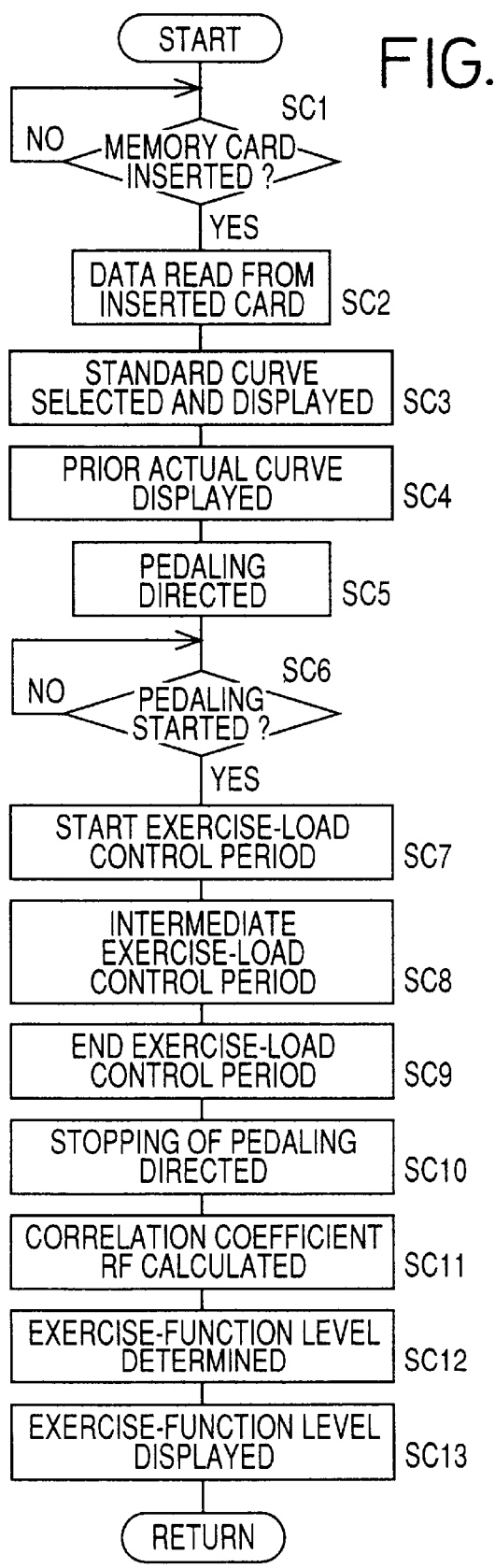
FIG. 10 is a flow chart representing an exercise-load control routine according to which the control device of the apparatus of FIG. 8 operates for changing an exercise load applied to a person by an ergometer.

The correlation-coefficient calculating means 126 calculates, according to a known mathematical expression, a correlation coefficient, RF, between the current actual curve 120 and the standard curve 116. The display control device 118 controls the display device 36 to display, in a display section 128 on the screen 37, an exercise-function level based on the correlation coefficient RF calculated by the calculating means 126. The exercise-function level may be the correlation coefficient RF itself, or an exercise-function index value corresponding to the coefficient RF. FIG. 9 shows the display section 128 in which a third class of an "A" level is indicated as the exercise-function level.

Next, there will be described the operation of the control device 109 of the exercise apparatus as the second embodiment. The control device 109 operates according to the flow charts of FIGS. 6 and 10. However, the description of the flow chart of FIG. 6 is omitted since it has already been described with respect to the first embodiment.

First, at Step SC1, a CPU 30 of the control device 109 judges whether a memory card 63 has been inserted in the card write/read device 64. If a negative judgment is made at Step SC1, Step SC1 is repeated. On the other hand, if a positive judgment is made at Step SC1, the control of the CPU 30 goes to Step SC2 to read in the data recorded on the memory card 63, and then goes to Step SC3 to select, from the different standard curves pre-stored in the ROM 32, a standard curve 116 corresponding to the data read from the card 63, i.e., age, sex, weight, and exercise-function level of the patient who possesses the card 63. Step SC3 corresponds to the standard-curve selecting means 114. Step SC3 is followed by Step SC4 to control the display device 36 to display, on the image screen 37, the selected standard curve 116 and a prior actual curve 121 obtained in a prior exercise test and recorded on the card 63. Step SC4 corresponds to the display control means 118.

Subsequently, the control of the CPU 30 goes to Step SC5 to issue, to the patient, a message "PLEASE PEDAL ERGOMETER TILL YOU ARE DIRECTED TO STOP" as a voice or an indication on the display device 36. Step SC5 is followed by Step SC6 to judge whether the patient has started pedaling the ergometer 6. If a negative judgment is made at Step SC6, Step SC6 is repeated. On the other hand, if a positive judgment is made at Step SC6, the control of the CPU 30 goes to Steps SC7, SC8, and SC9 to control the exercise load applied to the patient by the ergometer 6. Steps SC7, SC8, and SC9 correspond to the exercise-load control means 110. More specifically, at Step SC7, i.e., during a start period A shown in FIG. 5, the CPU 30 controls the generator 68 so that the ergometer 6 applies no exercise load to the patient, thereby letting him or her to rotate easily the pedals 65 of the ergometer 6. At Step SC8, i.e., during an intermediate period B, the ergometer 6 applies an exercise load which increases as time elapses at a predetermined rate according to a predetermined exercise-load pattern. At Step SC9, i.e., during an end period C, the ergometer 6 applies no exercise load again. The CPU 30 selects, from a plurality of different exercise-load patterns pre-stored in the ROM 32, a pattern corresponding to the age, sex, weight, and exercise-function level of the patient, as it selects the standard curve 116.

Figure 11:
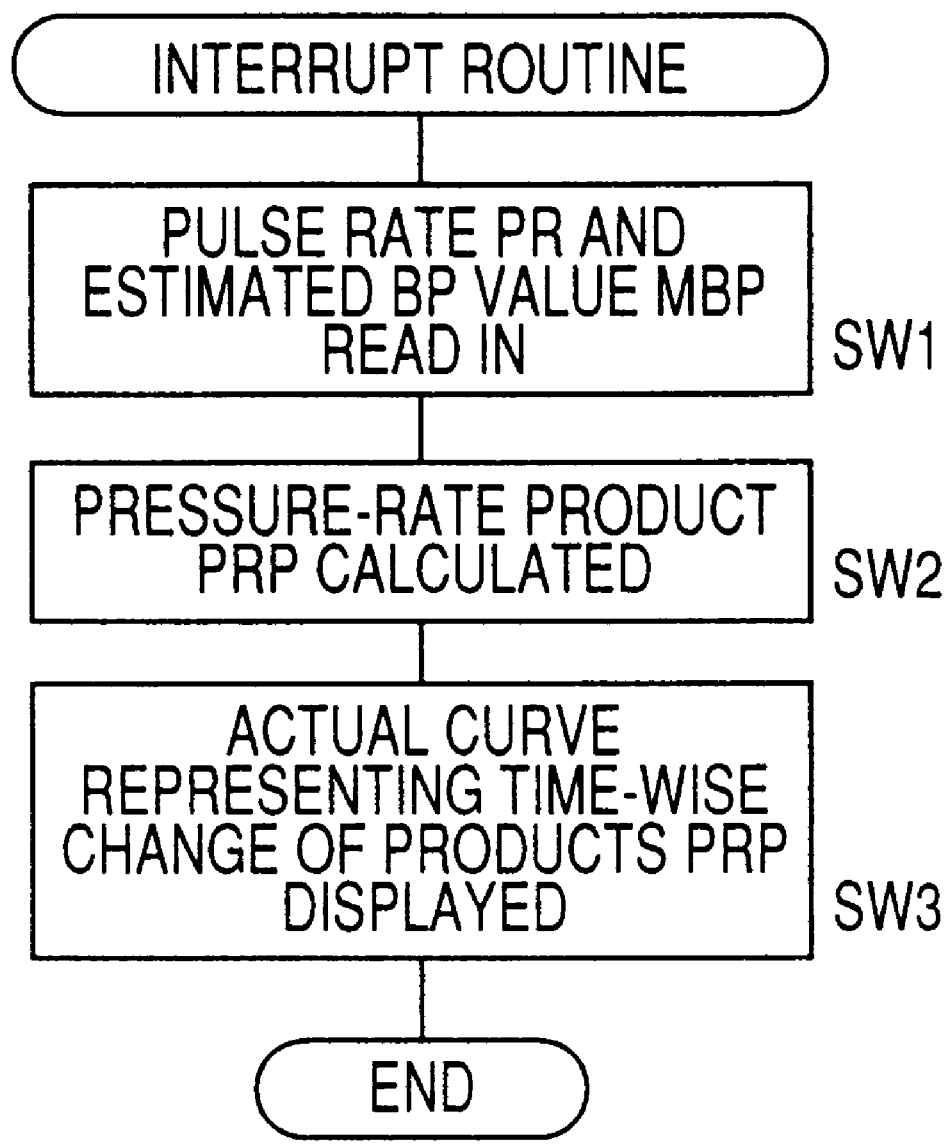
FIG. 11 is a flow chart representing an interrupt routine employed in the apparatus of FIG. 8.

An interrupt routine represented by the flow chart of FIG. 11 is started each time an actual pulse rate PR is determined and a systolic BP value $MBP_{SYS}$ is estimated according to the successive BP measurement routine of FIG. 6 while Steps SC7, SC8, and SC9 are carried out. At Step SW1 of the interrupt routine, the CPU 30 reads in the estimated systolic BP value $MBP_{SYS}$ and actual pulse rate PR obtained for one heartbeat-synchronous pulse of the PPW signal $SM_2$ and, at Step SW2, the CPU 30 calculates a pressure-rate product PRP ($=MBP_{SYS} \times PR$) by multiplying the estimated systolic BP value $MBP_{SYS}$ by the actual pulse rate PR. Step SW2 corresponds to the PRP calculating means 82. As Steps SW1 and SW2 are repeated, the CPU 30 controls, at Step SW3, the display device 36 to display the current actual curve 120 representing the actual pressure-rate products PRP, i.e., physical response of the patient who is undergoing the exercise load applied by the ergometer 6, so that the actual curve 120 grows or extends little by little on the image screen 37. Step SW3 corresponds to the display control means 118. FIG. 9 shows the state in which the exercise-load control in accordance with Steps SC7, SC8, and SC9 has just been ended.

Subsequently, the control of the CPU 30 goes to Step SC10 to output, to the patient, a message "PLEASE STOP PEDALING ERGOMETER" as a voice or an indication on the display device 36. In response to this message, the patient stops rotating the pedals 65 of the ergometer 6. Step SC10 is followed by Step SC11 corresponding to the correlation-coefficient calculating means 126.

At Step SC11, the CPU 30 calculates a correlation coefficient RF between the current actual curve 120 and the standard curve 116, according to a known mathematical expression. Step SC11 is followed by Step SC12 to determine the thus calculated correlation coefficient RF itself as an evaluation value indicative of the exercise function of the patient, or selects one of a predetermined number of ranks (A rank, B rank, . . . ) and degrees (1, 2, . . . ) of exercise-function levels which corresponds to the calculated correlation coefficient RF. Step SC12 is followed by Step SC13 to display the thus determined exercise-function level (e.g., A-3 shown in FIG. 9) in the display section 128 on the image screen 37. Steps SC12 and SC13 correspond to the display control means 118. In addition, the exercise-function level and the current actual curve 120 obtained in the current exercise test are recorded on the memory card 63 by the card write/read device 64.

As is apparent from the foregoing description relating to the exercise apparatus as the second embodiment, the display device 36 simultaneously displays an actual curve representing an actual time-wise change of pressure-rate products PRP successively calculated by the PRP calculating means 82, and a standard curve 116 corresponding to physical characteristics of a person being tested, in a common orthogonal coordinate system defined by the time axis 122 and the PRP axis 124. Thus, an observer such as a doctor or a nurse can compare the two curves 120, 116 each other. Since the pressure-rate product PRP as the product of pulse rate PR and blood pressure $MBP_{SYS}$ accurately indicate the internal load being applied to the person, the observer can evaluate with high accuracy the person's exercise function by the comparison of the two curves 120, 116.

In addition, the blood-pressure (BP) measuring means 78 successively and non-invasively measures the BP values of the person in synchronism with the heartbeat of the person, and accordingly the PRP calculating means 82 successively calculates the pressure-rate products PRP in synchronism with the heartbeat of the patient. That is, the BP measuring means 78 obtains a sufficiently great number of BP values which are utilized for providing the actual curve 120 to be compared with the standard curve 116. Therefore, the observer who may be the person being tested can evaluate the person's exercise function with high accuracy.

Additionally, the display device 36 displays a prior actual curve 121 recorded on the memory card 63, in addition to the standard curve 116 and a current actual curve 120 representing an actual time-wise change of pressure-rate products PRP successively calculated by the PRP calculating means 82 in a current exercise-function evaluation. Thus, the observer can compare the three curves 116, 120, 121 with one another, and can see the difference between the two actual curves 120, 121 and thereby recognize the change of the person's exercise function.

In the second embodiment, the display device 36 or display section 128 displays an evaluate value or level (e.g., A-3 in FIG. 9) of the exercise function of the person based on a correlation coefficient RF between the standard curve 116 and the actual curve 120 representing the actual time-wise change of the pressure-rate products PRP. Since the pressure-rate products PRP accurately indicate the internal load applied to the person, the evaluated value displayed by the display device 36 accurately indicates the exercise function of the person. In addition, the BP measuring means 78 successively and non-invasively measures the BP values of the person in synchronism with the heartbeat of the person, and accordingly the PRP calculating means 82 successively calculates the products PRP in synchronism with the heartbeat of the patient. That is, the BP measuring means 78 measures a sufficiently great number of BP values which are utilized for providing the actual curve 120. Therefore, the exercise function of the person can be evaluated with high accuracy based on the correlation coefficient RF.

In the second embodiment, at Step SW3, the control device 109 or the display control means 118 controls the display 36 to display, on the image screen 37, the actual curve 120 representing the time-wise change of the pressure-rate products PRP, while the patient undergoes the exercise test. Since the actual curve 120 grows or extends little by little as time elapses, the person is encouraged to continue his or her monotonous pedaling work in the exercise test.

Figure 12:
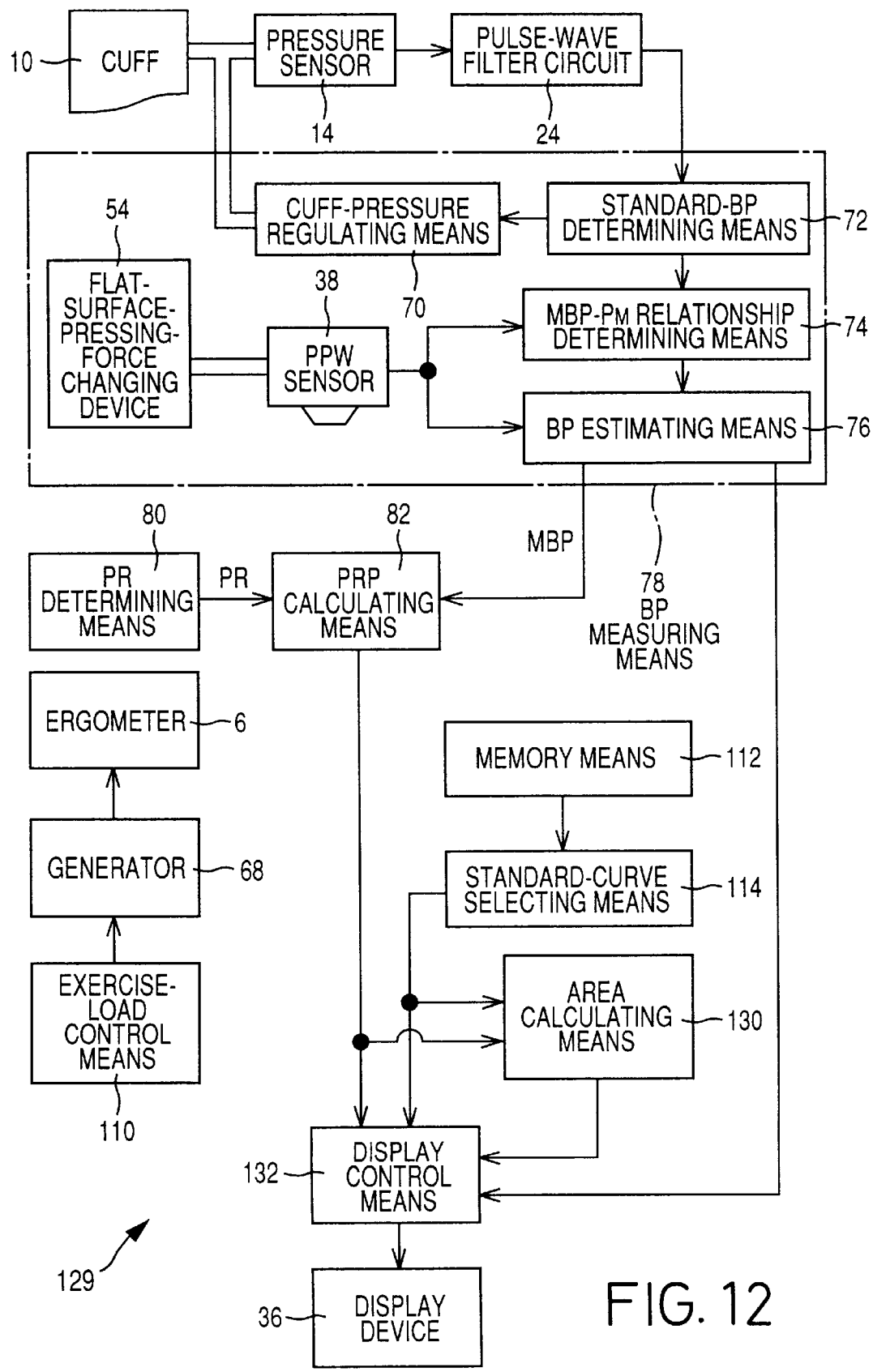
FIG. 12 is a block diagram corresponding to FIG. 3, for explaining various functions of a control device of another exercise apparatus as a third embodiment of the present invention.
Figure 13:
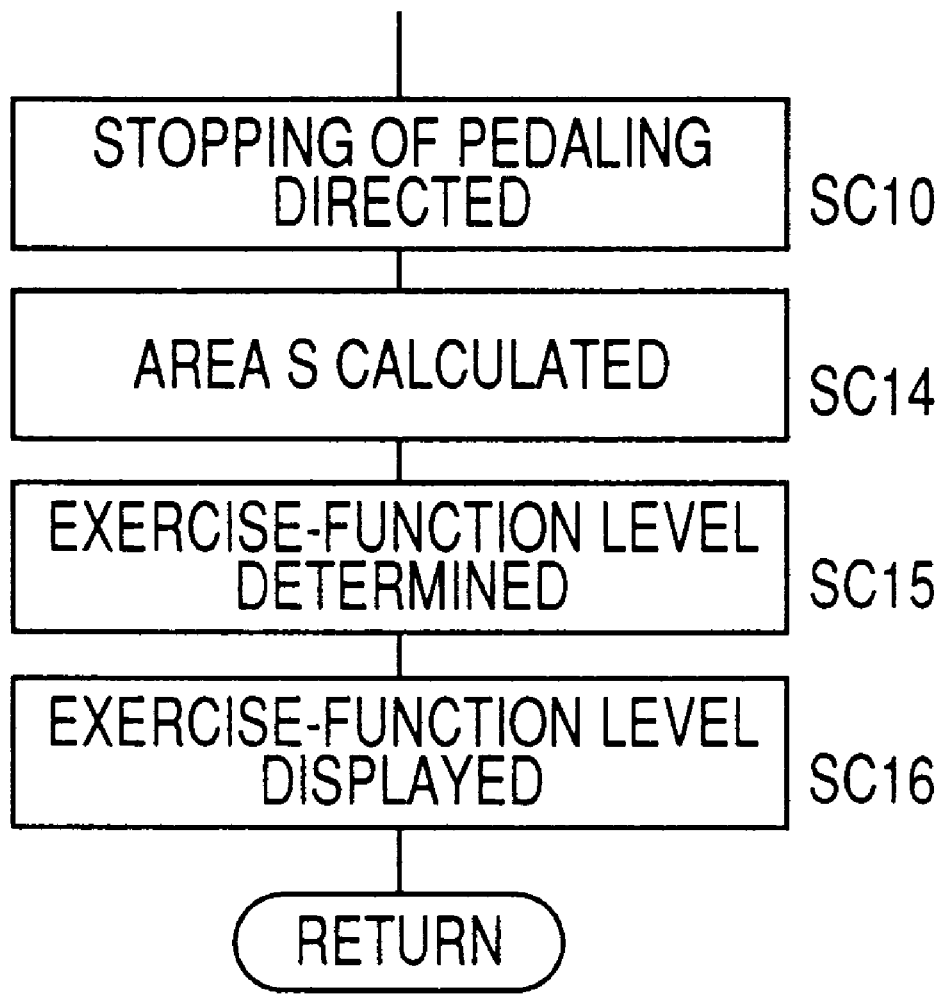
FIG. 13 is a flow chart representing an exercise-load control routine according to which the control device of the apparatus of FIG. 12 operates for changing an exercise load applied to a person by an ergometer.

Referring next to FIGS. 12 and 13, there will be described a third embodiment of the present invention. The third embodiment also relates to an exercise apparatus having the same hardware construction as that of the exercise apparatus 4 shown in FIG. 1, except that the third exercise apparatus includes a control device 129 shown in FIG. 12 in place of the control device 28 shown in FIG. 3 or the control device 109 shown in FIG. 8. The control device 129 of FIG. 12 is different from the control device 109 of FIG. 8 only in that the control device 129 functions as an area calculating means 130 and a display control means 132. The same reference numerals as used in the first and second embodiments are used to designate the corresponding elements or means of the third embodiment and the description thereof is omitted from the following description, which relates to only the differences between the second and third embodiments.

The area calculating means 130 calculates an area, S (FIG. 9), defined by, and between, an actual curve 120 representing an actual time-wise change of pressure-rate products PRP successively calculated by a PRP calculating means 82, and a standard curve 116 corresponding to physical characteristics of a person being tested, in a common orthogonal coordinate system defined by a time axis 122 and a PRP axis 124. The area S is obtained within an intermediate exercise-load control period B. More specifically, a CPU 30 of the control device 129 subtracts, from each of the actual pressure-rate products PRP of the actual curve 120, a corresponding one of standard pressure-rate products PRP of the standard curve 116, and sums up the thus obtained differences, within the intermediate period B.

The display control means 132 controls a display device 36 to display, in a display section 128 on an image screen 37, the area value S calculated by the area calculating means 130, or an evaluated exercise-function value corresponding to the area value S.

Next, there will be described the operation of the control device 129 of the exercise apparatus as the third embodiment. The control device 129 operates according to the flow charts of FIGS. 6 and 13. However, the description of the flow chart of FIG. 6 is omitted since it has already been described with respect to the first embodiment. The flow chart of FIG. 13 is basically similar to the flow chart of FIG. 10 and is different from the latter only in that the flow chart of FIG. 13 includes Steps SC14, SC15, and SC16 in place of Steps SC11, SC12, and SC13 of FIG. 10. The description of Steps SC1 to SC10 is omitted.

At Step SC14, the CPU 30 calculates an area S defined by, and between, the actual curve 120 and the standard curve 116, in the orthogonal coordinate system defined by the time axis 122 and the PRP axis 124, in the manner as described above. Step SC14 corresponds to the area calculating means 130.

Step SC14 is followed by Step SC15 to determine the thus calculated area S itself as an evaluation value indicative of the exercise function of the patient, or selects one of a predetermined number of ranks (A rank, B rank, . . . ) and degrees (1, 2, . . . ) of exercise-function levels which corresponds to the calculated area S. Step SC14 is followed by Step SC15 to display the thus determined exercise-function level (e.g., A-3 shown in FIG. 9) in the display section 128 on the image screen 37. Steps SC14 and SC15 correspond to the display control means 132. In addition, the exercise-function level and the current actual curve 120 obtained in the current exercise test are recorded on a memory card 63 by a card writing and reading device 64.

As is apparent from the foregoing description relating to the exercise apparatus as the third embodiment, the display device 36 displays an evaluation value of the exercise function of a person based on an area S defined by, and between, the standard curve 116 and the actual curve 120 representing the actual time-wise change of the pressure-rate products PRP successively calculated by the PRP calculating means 82. Since the pressure-rate products PRP accurately indicate the internal load applied to the person, the evaluation value displayed by the display device 36 accurately indicates the exercise function of the person.

In addition, the BP measuring means 78 successively and non-invasively measures the BP values of the person in synchronism with the heartbeat of the person, and accordingly the PRP calculating means 82 successively calculates the pressure-rate products PRP in synchronism with the heartbeat of the patient. That is, the BP measuring means 78 obtains a sufficiently great number of BP values which are utilized for providing the actual curve 120 which in turn is used for calculating the area S. Therefore, the exercise function of the person can be evaluated with high accuracy based on the accurate area S.

While the present invention has been described in its preferred embodiment, the present invention may otherwise be embodied.

Figure 14:
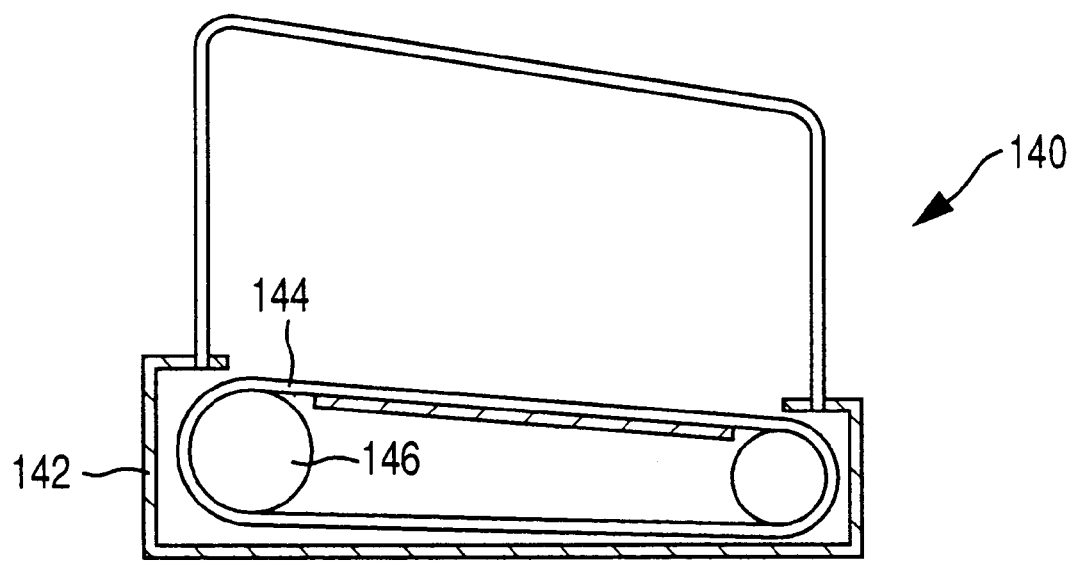
FIG. 14 is a view of a treadmill as an exercise-load applying device employed in another exercise apparatus as a fifth embodiment of the present invention.

For example, although in the illustrated embodiments the ergometer 6 is employed as the exercise-load applying device, the ergometer 6 may be replaced by a treadmill 140 as shown in FIG. 14. The treadmill 140 includes a base member 142 which supports an endless belt 144 such that the belt 144 is moved or circulated by an electric motor 146 while a person walks or runs on the moving belt 144. In this case, the control device 28, 109, 129 supplies a command single to the electric motor 146 so that the motor 146 changes the speed of movement or circulation of the belt 144, thereby changing the exercise load applied to the person. Thus, the electric motor 146 functions as the exercise-load changing device, like the generator 68.

In the first embodiment shown in FIG. 5, the display device 36 indicates, in the first section 98, the prior and current total energy values WH by using the bar graph 102, 104, 106. However, it is possible to display the total energy values WH in other manners, e.g., using a polygonal graph. In addition, a three-dimensional effect may be added to each of the bars 102, 104, 106, so that an observer may see the change of the values WH more easily.

In each of the illustrated embodiments, the card read/write device 64 may be replaced by a keyboard through which various data may be input to the control device 28, 109, 129.

In each illustrated embodiment, the control device 28 functions as the PR determining means 80 which determines the PR values of the patient from the difference between the respective times of occurrence of each pair of successive heartbeat-synchronous pulses of the PPW signal $SM_2$ supplied from the PPW sensor 38. However, the PPW signal $SM_2$ may be replaced by a photoelectric pulse wave signal produced by a blood-oxygen-saturation sensor as one of photoelectric pulse wave sensors, or an impedance pulse wave signal produced by an impedance pulse wave sensor.

In each embodiment, the BP measuring device 8 or the BP measuring means 78 may be replaced by a different device which includes a volumetric pulse wave sensor, as one of photoelectric pulse wave sensors, which detects a volumetric pulse wave from a person; means for determining a relationship between (a) blood pressure and (b) area defined by a heartbeat-synchronous pulse of volumetric pulse wave; and means for estimating a BP value of the person based on the area defined by each of successive heartbeat-synchronous pulses of the volumetric pulse wave detected by the sensor according to the determined relationship.

While in each illustrated embodiment the BP measuring means 78 measures BP values MBP of a patient for each of heartbeat-synchronous pulses of the PPW signal $SM_2$, the BP measuring means 78 may be modified to measure one or more BP values MBP of a patient for every second, third, fourth, . . . heartbeat-synchronous pulse of the PPW signal $SM_2$.

Although in each illustrated embodiment the relationship determining means 74 determines, as the MBP-$P_M$ relationship, the linear function defined by the expression (1), the relationship determining means 74 may be modified to determine, as the MBP-$P_M$ relationship, a quadratic or higher-order function which may include, if necessary, a correction term.

Although in each illustrated embodiment the standard-BP determining means 72 determines one or more standard BP values of the patient based on the variation of the CPW $SM_1$ obtained while the cuff pressure $P_c$ is slowly decreased, the standard-BP determining means 72 may be modified to determine one or more standard BP values of a person based on the variation of the CPW $SM_1$ obtained while the cuff pressure $P_c$ is slowly increased.

While in each illustrated embodiment the standard-BP determining means 72 determines one or more standard BP values of the patient according to a known oscillometric method, the standard-BP determining means 72 may be replaced by a different BP measuring device which also includes a cuff and a device for chaining the cuff pressure and which determines, according to a known Korotkoff method, one or more standard BP values of a person based on a cuff pressure at the time when a Korotkoff sound is first detected, and/or last detected, from person's body portion (e.g., upper arm) being pressed under the cuff while the cuff pressure is changed by the cuff-pressure changing device.

It is to be understood that the present invention may be embodied with other changes, improvements, and modifications that may occur to those skilled in the art without departing from the spirit and scope of the invention defined in the appended claims.

What is claimed is:

1. An apparatus for evaluating an exercise function of a person who undergoes an exercise load, comprising:

a pulse-rate measuring device which successively measures a pulse rate of the person in synchronism with a heartbeat of the person;

a blood-pressure measuring device which successively and non-invasively measures a blood pressure of the person in synchronism with the heartbeat of the person;

a first calculating device which successively calculates a pressure rate product of said pulse rate and said blood pressure a in synchronism with the heartbeat of the person;

a second calculating device which calculates a total energy produced by the person after application of the exercise load to the person is started and before the products successively calculated by said first calculating device increase up to a target value; and a display device which displays an evaluation value of the exercise function of the person based on the total energy calculated by said second calculating device.

2. An apparatus according to claim 1, wherein said blood-pressure measuring device comprises:

a pressing device which provides a pressing force to press a body portion of the person;

a pressing-force changing device which changes the pressing force of said pressing device;

standard-blood-pressure determining means for determining a standard blood pressure of the person based on a heartbeat-synchronous wave obtained while the pressing force of said pressing device is changed by said pressing-force changing device;

a pressure-pulse-wave sensor adapted to be pressed against an artery of the person via a skin tissue above the artery so as to detect a magnitude of a pressure pulse wave produced from the artery in synchronism with the heartbeat of the person;

relationship determining means for determining a relationship between blood pressure and magnitude of pressure pulse wave, based on the standard blood pressure determined by said standard-blood-pressure determining means and the magnitude of the pressure pulse wave detected by said pressure pulse wave sensor; and blood-pressure estimating means for successively estimating a blood pressure of the person, based on a magnitude of each of a plurality of heartbeat-synchronous pulses of the pressure pulse wave detected by said pressure pulse wave sensor, according to the relationship determined by said relationship determining means.

3. An apparatus according to claim 2, wherein said pressing device comprises an inflatable cuff adapted to be wound around the body portion of the person, said pressing-force changing device comprising a cuff-pressure changing device which changes a fluid pressure in said cuff, said standard-blood-pressure determining means comprising means for determining the standard blood pressure of the person based on a variation of respective amplitudes of a plurality of heartbeat-synchronous pulses of the heartbeat-synchronous wave which is a pressure oscillation produced in said cuff while the pressure of the cuff is changed by said cuff-pressure changing device.

4. An apparatus according to claim 2, wherein said pressing device comprises an inflatable cuff adapted to be wound around the body portion of the person, said pressing-force changing device comprising a cuff-pressure changing device which changes a fluid pressure in said cuff, said standard-blood-pressure determining means comprising means for determining the standard blood pressure of the person based on a fluid pressure of said cuff at a time when a Korotkoff sound is first detected, or last detected, from the body portion while the pressure of the cuff is changed by said cuff-pressure changing device.

5. An apparatus according to claim 2, wherein said pressure pulse wave sensor comprises a flat surface adapted to be pressed against the artery of the person via the skin tissue, a plurality of pressure sensing elements arranged in the flat surface, and a flat-surface pressing device which presses the flat surface against the artery via the skin tissue, and wherein said blood-pressure measuring device comprises means for controlling the flat-surface pressing device to press the flat surface against the artery via the skin tissue such that a portion of a wall of the artery is flattened under the flat surface and the skin tissue.

6. An apparatus according to claim 2, wherein said standard-blood-pressure determining means comprises means for determining the standard blood pressure of the person, before the application of the exercise load to the person is started, and wherein said relationship determining means comprises means for determining the relationship between blood pressure and magnitude of pressure pulse wave, based on the standard blood pressure determined by the standard-blood-pressure determining means and the magnitude of the pressure pulse wave detected by said pressure pulse wave sensor before the application of the exercise load to the person is started.

7. An apparatus according to claim 1, further comprising:

an exercise-load applying device which applies the exercise load to the person;

an exercise-load changing device which changes the exercise load applied to the person by said exercise-load applying device; and judging means for judging whether the products successively calculated by said first calculating device have increased up to the target value, said exercise-load changing device zeroing, when said judging means makes a positive judgment, the exercise load applied to the person by said exercise-load applying device.

8. An apparatus according to claim 7, wherein said exercise-load applying device comprises a generator which includes a rotary member and which generates an electric power when said rotary member is rotated by the person, and wherein said second calculating device comprises means for calculating said total energy based on a total energy produced by said generator after the application of the exercise load to the person is started and before the products successively calculated by said first calculating device increase up to the target value.

9. An apparatus according to claim 1, wherein said display device comprises means for displaying said evaluation value comprising at least one of said total energy calculated by said second calculating device and an exercise-function index value corresponding to said total energy.

10. An apparatus for evaluating an exercise function of a person who undergoes a predetermined exercise load, comprising:

a pulse-rate measuring device which successively measures a pulse rate of the person in synchronism with a heartbeat of the person;

a blood-pressure measuring device which successively and non-invasively measures a blood pressure of the person in synchronism with the heartbeat of the person;

a calculating device which successively calculates a pressure-rate product as a product of said pulse rate and said blood pressure, in synchronism with the heartbeat of the person;

a first memory device which stores a first curve which represents a standard time-wise change of pressure-rate products and which corresponds to said predetermined exercise load; and a display device which simultaneously displays said first curve and a second curve representing an actual time-wise change of the pressure-rate products successively calculated by said calculating device, so that an observer can compare said first curve and said second curve with each other.

11. An apparatus according to claim 10, wherein said blood-pressure measuring device comprises:

a pressing device which provides a pressing force to press a body portion of the person;

a pressing-force changing device which changes the pressing force of said pressing device;

standard-blood-pressure determining means for determining a standard blood pressure of the person based on a heartbeat-synchronous wave obtained while the pressing force of said pressing device is changed by said pressing-force changing device;

a pressure-pulse-wave sensor adapted to be pressed against an artery of the person via a skin tissue above the artery so as to detect a magnitude of a pressure pulse wave produced from the artery in synchronism with the heartbeat of the person;

relationship determining means for determining a relationship between blood pressure and magnitude of pressure pulse wave, based on the standard blood pressure determined by said standard-blood-pressure determining means and the magnitude of the pressure pulse wave detected by said pressure pulse wave sensor; and blood-pressure estimating means for successively estimating a blood pressure of the person, based on a magnitude of each of a plurality of heartbeat-synchronous pulses of the pressure pulse wave detected by said pressure pulse wave sensor, according to the relationship determined by said relationship determining means.

12. An apparatus according to claim 11, wherein said pressing device comprises an inflatable cuff adapted to be wound around the body portion of the person, said pressing-force changing device comprising a cuff-pressure changing device which changes a fluid pressure in said cuff, said standard-blood-pressure determining means comprising means for determining the standard blood pressure of the person based on a variation of respective amplitudes of a plurality of heartbeat-synchronous pulses of the heartbeat-synchronous wave which is a pressure oscillation produced in said cuff while the pressure of the cuff is changed by said cuff-pressure changing device.

13. An apparatus according to claim 11, wherein said pressing device comprises an inflatable cuff adapted to be wound around the body portion of the person, said pressing-force changing device comprising a cuff-pressure changing device which changes a fluid pressure in said cuff, said standard-blood-pressure determining means comprising means for determining the standard blood pressure of the person based on a fluid pressure of said cuff at a time when a Korotkoff sound is first detected, or last detected, from the body portion while the pressure of the cuff is changed by said cuff-pressure changing device.

14. An apparatus according to claim 11, wherein said pressure pulse wave sensor comprises a flat surface adapted to be pressed against the artery of the person via the skin tissue, a plurality of pressure sensing elements arranged in the flat surface, and a flat-surface pressing device which presses the flat surface against the artery via the skin tissue, and wherein said blood-pressure measuring device comprises means for controlling the flat-surface pressing device to press the flat surface against the artery via the skin tissue such that a portion of a wall of the artery is flattened under the flat surface and the skin tissue.

15. An apparatus according to claim 11, wherein said standard-blood-pressure determining means comprises means for determining the standard blood pressure of the person, before the application of the exercise load to the person is started, and wherein said relationship determining means comprises means for determining the relationship between blood pressure and magnitude of pressure pulse wave, based on the standard blood pressure determined by the standard-blood-pressure determining means and the magnitude of the pressure pulse wave detected by said pressure pulse wave sensor before the application of the exercise load to the person is started.

16. An apparatus according to claim 10, further comprising a second memory device which stores said second curve, wherein said display device comprises means for displaying said second curve stored in said second memory device, in addition to said first curve and a following second curve representing an actual time-wise change of pressure-rate products successively calculated by said calculating device in a following exercise-function evaluation, so that the observer can compare said second curve, said first curve, and said following second curve with one another.

17. An apparatus according to claim 10, further comprising:

an exercise-load applying device which applies an exercise load to the person; and an exercise-load changing device which changes the exercise load applied to the person by said exercise-load applying device, to said predetermined exercise load, according to a predetermined exercise-load pattern.

18. An apparatus for evaluating an exercise function of a person who undergoes a predetermined exercise load, comprising:

a pulse-rate measuring device which successively measures a pulse rate of the person in synchronism with a heartbeat of the person;

a blood-pressure measuring device which successively and non-invasively measures a blood pressure of the person in synchronism with the heartbeat of the person;

a calculating device which successively calculates a pressure-rate product as a product of said pulse rate and said blood pressure, in synchronism with the heartbeat of the person;

a memory device which stores a first curve which represents a standard time-wise change of pressure-rate products and which corresponds to said predetermined exercise load; and a display device which displays an evaluation value of the exercise function of the person based on a correlation coefficient between said first curve and a second curve representing an actual time-wise change of the pressure-rate products successively calculated by said calculating device.

19. An apparatus according to claim 18, wherein said display device comprises means for displaying said evaluation value comprising at least one of said correlation coefficient between said first curve and said second curve and an exercise-function index value corresponding to said correlation coefficient.

20. An apparatus for evaluating an exercise function of a person who undergoes a predetermined exercise load, comprising:

a pulse-rate measuring device which successively measures a pulse rate of the person in synchronism with a heartbeat of the person;

a blood-pressure measuring device which successively and non-invasively measures a blood pressure of the person in synchronism with the heartbeat of the person;

a calculating device which successively calculates a pressure-rate product as a product of said pulse rate and said blood pressure, in synchronism with the heartbeat of the person;

a memory device which stores a first curve which represents a standard time-wise change of pressure-rate products and which corresponds to said predetermined exercise load; and a display device which displays an evaluation value of the exercise function of the person based on an area defined by, and between, said first curve and a second curve representing an actual time-wise change of the pressure-rate products successively calculated by said calculating device.

21. An apparatus according to claim 20, wherein said display device comprises means for displaying said evaluation value comprising at least one of said area defined by and between said first curve and said second curve and an exercise-function index value corresponding to said area.

* * * * *